(12) United States Patent
Shaolian et al.

(10) Patent No.: US 6,187,036 B1
(45) Date of Patent: Feb. 13, 2001

(54) ENDOLUMINAL VASCULAR PROSTHESIS

(75) Inventors: Samuel M. Shaolian, Newport Beach; M. Frank Zeng, Irvine, both of CA (US)

(73) Assignee: Endologix, Inc., Irvine, CA (US)

( * ) Notice: Under 35 U.S.C. 154(b), the term of this patent shall be extended for 0 days.

(21) Appl. No.: 09/210,280

(22) Filed: Dec. 11, 1998

(51) Int. Cl.$^7$ ..................................................... A61F 2/06
(52) U.S. Cl. ........................... 623/1.15; 623/1.13; 623/1.1
(58) Field of Search .................................... 623/1, 12, 11, 623/1.1, 1.13, 1.15; 606/194, 195, 198

(56) References Cited

U.S. PATENT DOCUMENTS

| | | |
|---|---|---|
| 2,127,903 | 8/1938 | Bowen . |
| 2,845,959 | 8/1958 | Sidebotham . |
| 2,990,605 | 7/1961 | Demsyk . |

(List continued on next page.)

FOREIGN PATENT DOCUMENTS

| | | |
|---|---|---|
| 0 177 330 B1 | 6/1991 | (EP) . |
| 0 621 015 A1 | 10/1994 | (EP) . |
| 0 747 020 A2 | 12/1996 | (EP) . |
| 0 775 470 A1 | 5/1997 | (EP) . |
| WO 93/13825 | 7/1993 | (WO) . |
| WO 96/41589 | 12/1996 | (WO) . |
| WO 97/10777 | 3/1997 | (WO) . |

* cited by examiner

Primary Examiner—Michael J. Milano
Assistant Examiner—Hieu Phan
(74) Attorney, Agent, or Firm—Knobbe, Martens, Olson & Bear, LLP

(57) ABSTRACT

Disclosed is a tubular endoluminal vascular prosthesis, useful in treating, for example, an abdominal aortic aneurysm. The prosthesis includes a self expandable wire support structure surrounded by a flexible tubular membrane. A delivery catheter and methods are also disclosed.

5 Claims, 23 Drawing Sheets

U.S. PATENT DOCUMENTS

| | | | |
|---|---|---|---|
| 3,029,819 | 4/1962 | Starks . | |
| 3,096,560 | 7/1963 | Liebig . | |
| 3,805,301 | 4/1974 | Liebig . | |
| 4,497,074 | 2/1985 | Rey et al. . | |
| 4,501,263 | 2/1985 | Harbuck . | |
| 4,503,568 | 3/1985 | Madras . | |
| 4,592,754 | 6/1986 | Gupte et al. . | |
| 4,617,932 | 10/1986 | Kornberg . | |
| 4,816,028 | 3/1989 | Kapadia et al. . | |
| 4,840,940 | 6/1989 | Sottiurai . | |
| 4,856,516 | 8/1989 | Hillstead . | |
| 4,878,906 | 11/1989 | Lindemann et al. . | |
| 4,907,336 | 3/1990 | Gianturco . | |
| 4,922,905 | 5/1990 | Strecker . | |
| 4,994,071 | 2/1991 | MacGregor . | |
| 5,019,090 | 5/1991 | Pinchuk . | |
| 5,078,726 | 1/1992 | Kreamer . | |
| 5,104,399 | 4/1992 | Lazarus . | |
| 5,108,424 | 4/1992 | Hoffman, Jr. et al. . | |
| 5,133,732 * | 7/1992 | Wiktor | 606/195 |
| 5,135,536 | 8/1992 | Hillstead . | |
| 5,156,619 | 10/1992 | Ehrenfeld . | |
| 5,178,634 | 1/1993 | Martinez . | |
| 5,197,976 | 3/1993 | Herweck et al. . | |
| 5,256,141 | 10/1993 | Gencheff et al. . | |
| 5,275,622 | 1/1994 | Lazarus et al. . | |
| 5,282,824 | 2/1994 | Gianturco . | |
| 5,304,200 | 4/1994 | Spaulding . | |
| 5,314,472 * | 5/1994 | Fontaine | 623/12 |
| 5,316,023 | 5/1994 | Palmaz et al. . | |
| 5,342,387 | 8/1994 | Summers . | |
| 5,360,443 | 11/1994 | Barone et al. . | |
| 5,366,504 | 11/1994 | Andersen et al. . | |
| 5,370,683 | 12/1994 | Fontaine . | |
| 5,387,235 | 2/1995 | Chuter . | |
| 5,405,377 | 4/1995 | Cragg . | |
| 5,423,886 | 6/1995 | Arru et al. . | |
| 5,425,765 | 6/1995 | Tiefenbrun et al. . | |
| 5,443,498 | 8/1995 | Fontaine . | |
| 5,443,500 | 8/1995 | Sigwart . | |
| 5,456,713 | 10/1995 | Chuter . | |
| 5,464,450 * | 11/1995 | Buscemi et al. | 623/6 |
| 5,489,295 | 2/1996 | Piplani et al. . | |
| 5,496,365 | 3/1996 | Sgro . | |
| 5,507,767 | 4/1996 | Maeda et al. . | |
| 5,507,771 | 4/1996 | Gianturco . | |
| 5,522,880 | 6/1996 | Barone et al. . | |
| 5,522,881 | 6/1996 | Lentz . | |
| 5,522,883 | 6/1996 | Slater et al. . | |
| 5,545,211 * | 8/1996 | An et al. | 623/1 |
| 5,554,181 | 9/1996 | Das . | |
| 5,562,728 | 10/1996 | Lazarus et al. . | |
| 5,578,072 | 11/1996 | Barone et al. . | |
| 5,591,229 | 1/1997 | Parodi . | |
| 5,609,625 | 3/1997 | Piplani et al. . | |
| 5,609,627 | 3/1997 | Giocoechea et al. . | |
| 5,609,628 * | 3/1997 | Keranen | 623/1 |
| 5,628,788 | 5/1997 | Pinchuk . | |
| 5,632,772 | 5/1997 | Alcime et al. . | |
| 5,643,339 | 7/1997 | Kavteladze et al. . | |
| 5,647,857 | 7/1997 | Anderson et al. . | |
| 5,653,727 | 8/1997 | Wiktor . | |
| 5,653,743 | 8/1997 | Martin . | |
| 5,653,746 | 8/1997 | Schmitt . | |
| 5,653,747 | 8/1997 | Dereume . | |
| 5,662,700 | 9/1997 | Lazarus . | |
| 5,662,702 | 9/1997 | Keranen . | |
| 5,665,115 | 9/1997 | Cragg . | |
| 5,665,117 | 9/1997 | Rhodes . | |
| 5,674,241 | 10/1997 | Bley et al. . | |
| 5,674,276 | 10/1997 | Andersen et al. . | |
| 5,676,696 | 10/1997 | Marcade . | |
| 5,676,697 | 10/1997 | McDonald . | |
| 5,679,400 | 10/1997 | Tuch . | |
| 5,681,346 | 10/1997 | Orth et al. . | |
| 5,683,448 | 11/1997 | Cragg . | |
| 5,683,449 | 11/1997 | Marcade . | |
| 5,683,450 | 11/1997 | Goicoechea et al. . | |
| 5,683,451 | 11/1997 | Lenker et al. . | |
| 5,683,452 | 11/1997 | Barone et al. . | |
| 5,683,453 | 11/1997 | Palmaz . | |
| 5,690,644 | 11/1997 | Yurek et al. . | |
| 5,693,066 | 12/1997 | Rupp et al. . | |
| 5,693,084 | 12/1997 | Chuter . | |
| 5,693,086 | 12/1997 | Goicoechea et al. . | |
| 5,693,087 | 12/1997 | Parodi . | |
| 5,693,088 | 12/1997 | Lararus . | |
| 5,695,516 | 12/1997 | Fischell et al. . | |
| 5,695,517 | 12/1997 | Marin et al. . | |
| 5,716,365 | 2/1998 | Giocoechea et al. . | |
| 5,716,393 | 2/1998 | Lindenberg et al. . | |
| 5,720,776 | 2/1998 | Chuter et al. . | |
| 5,723,004 | 3/1998 | Dereume et al. . | |
| 5,746,766 | 5/1998 | Edoga . | |
| 5,755,771 | 5/1998 | Penn et al. . | |
| 5,851,228 | 12/1998 | Pinheiro . | |
| 5,868,783 | 2/1999 | Tower . | |
| 5,893,887 | 4/1999 | Jayaraman . | |
| 5,906,640 | 5/1999 | Penn et al. . | |
| 5,919,225 * | 7/1999 | Lau et al. | 623/1 |
| 5,925,075 * | 7/1999 | Myers et al. | 623/1 |
| 5,948,018 | 9/1999 | Dereume et al. . | |

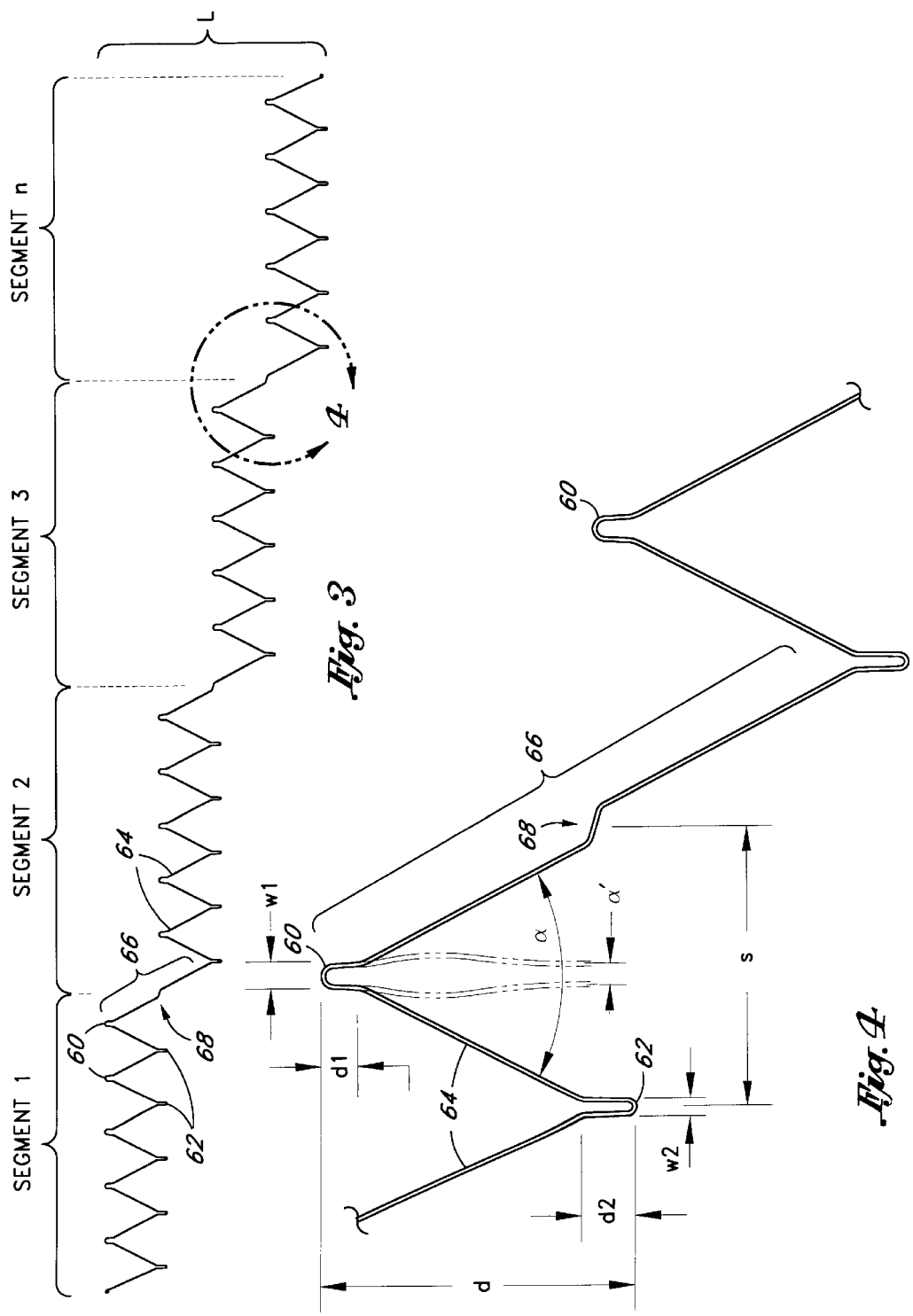

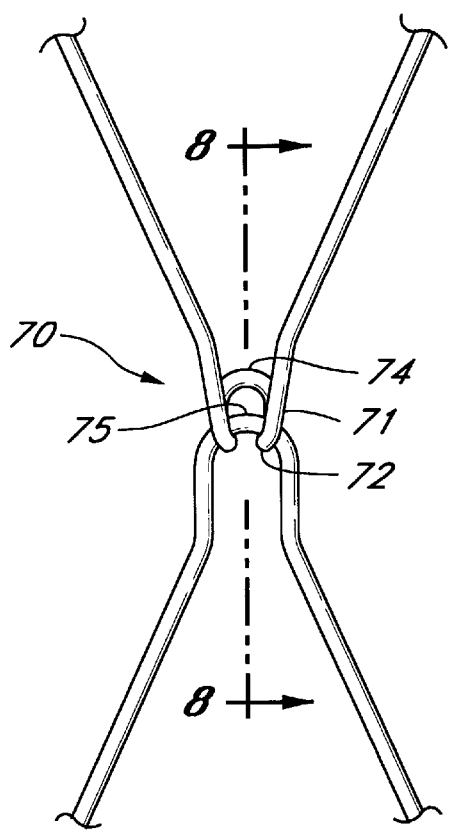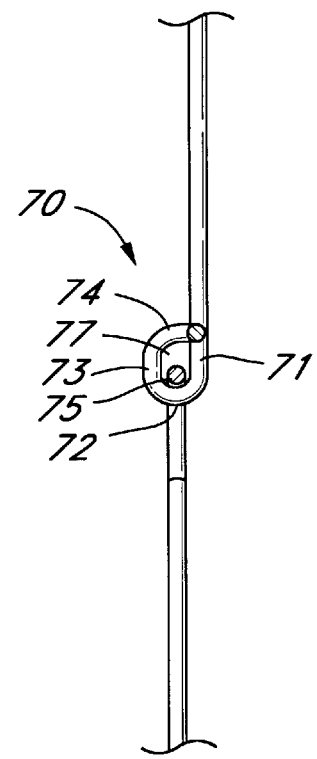

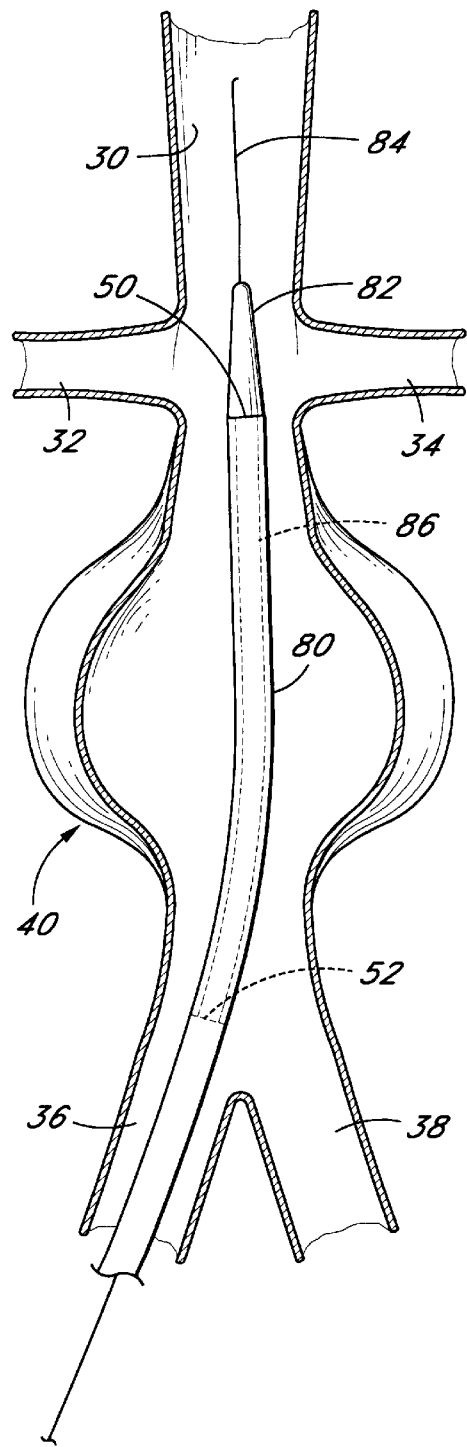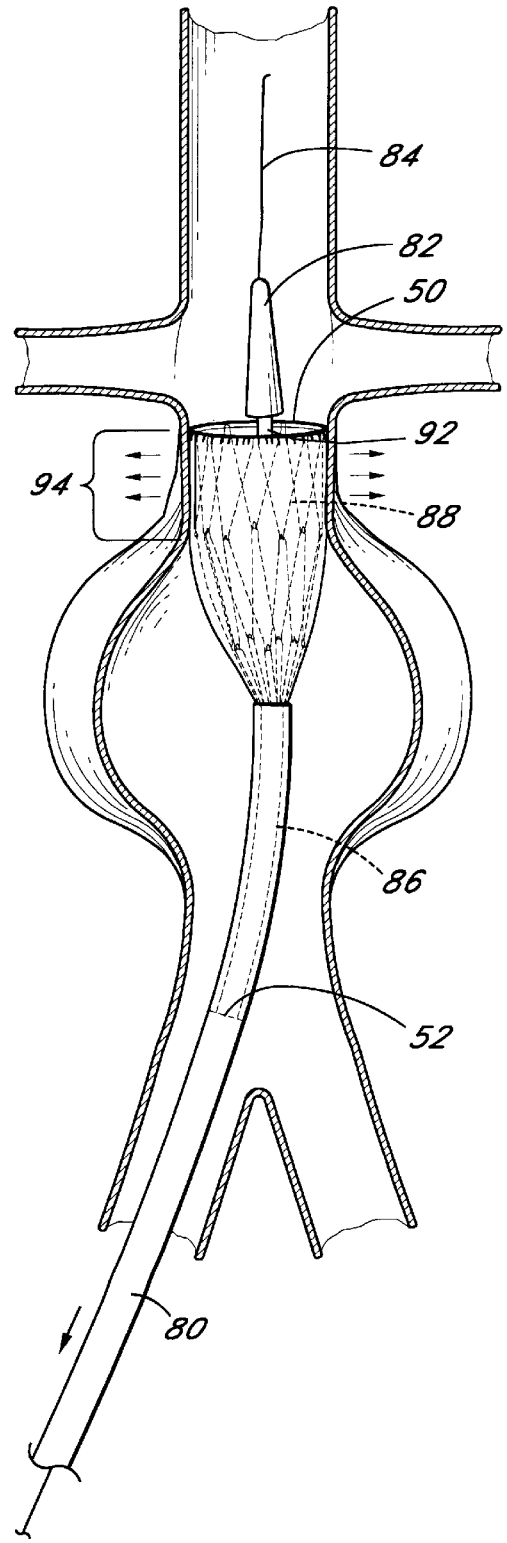

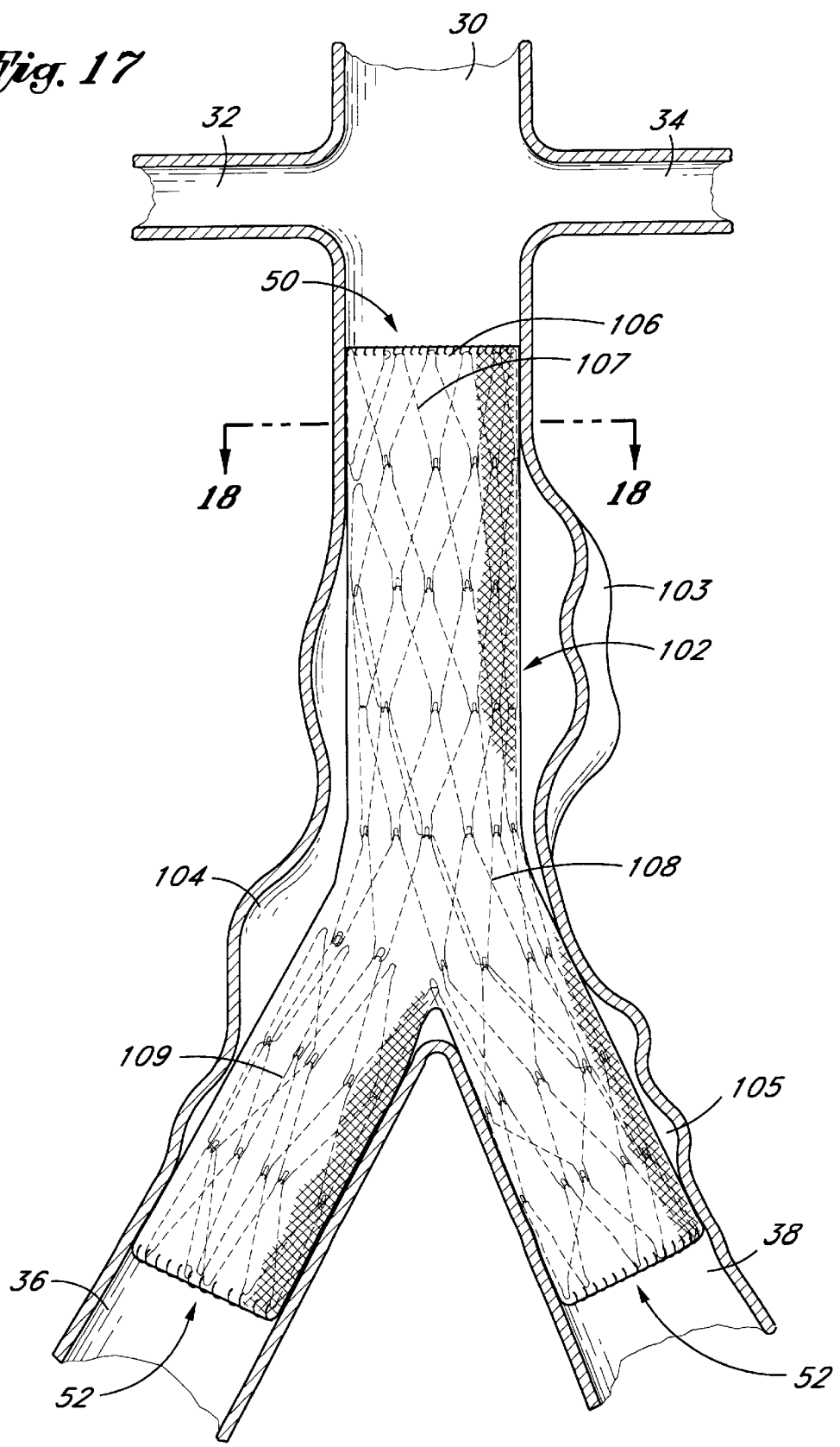

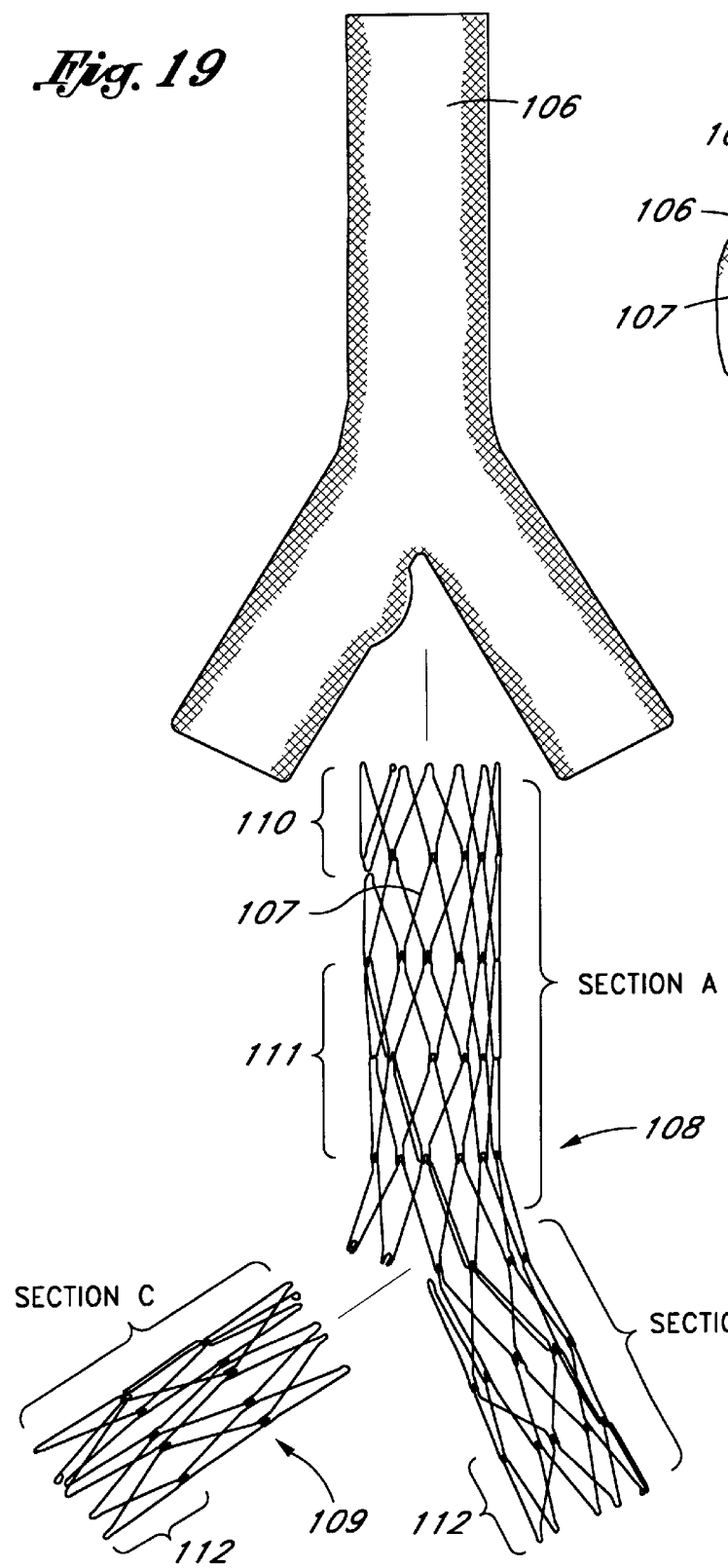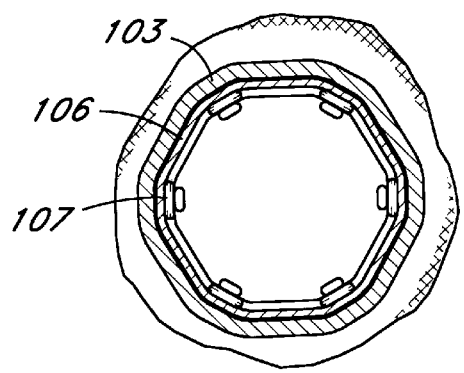

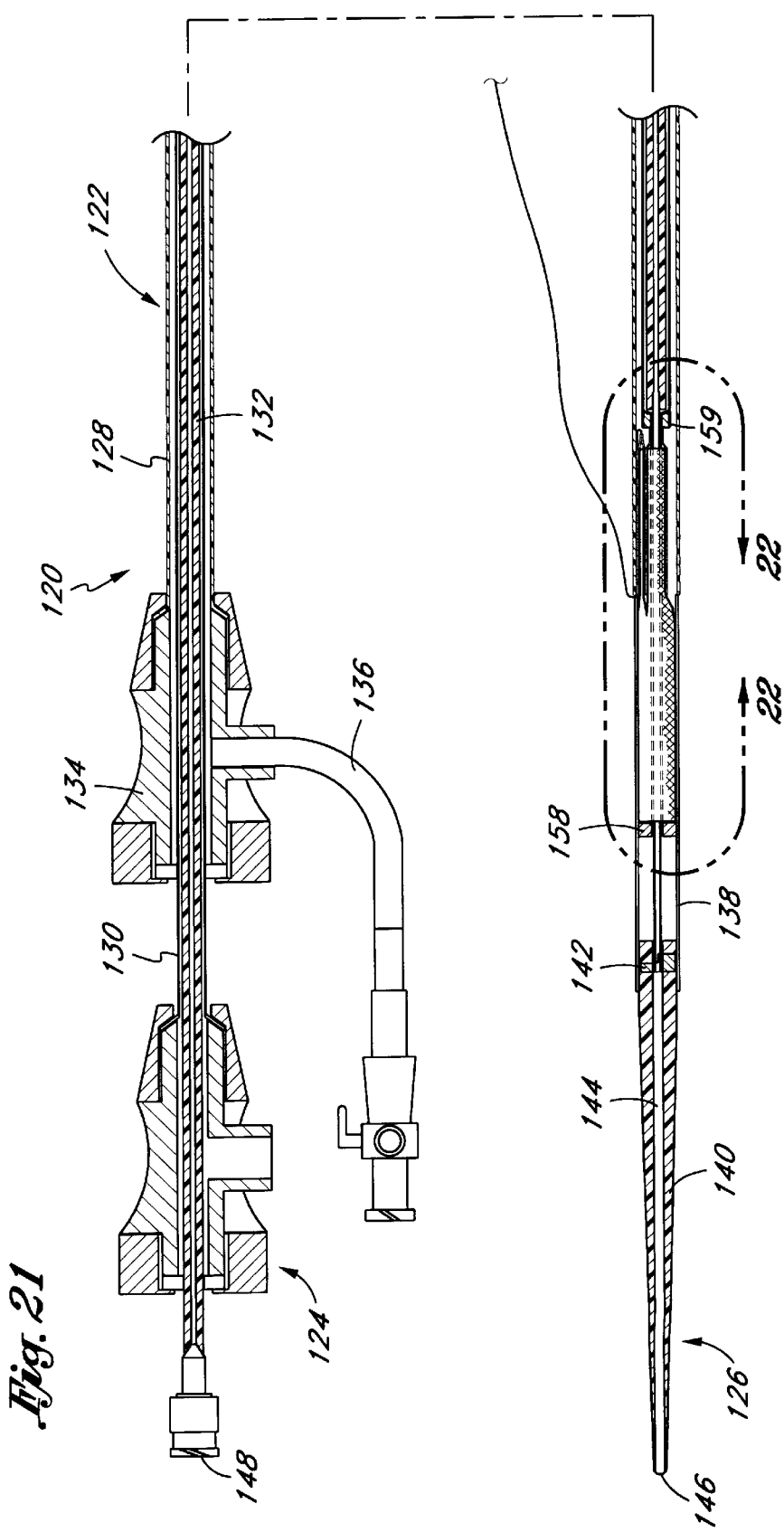

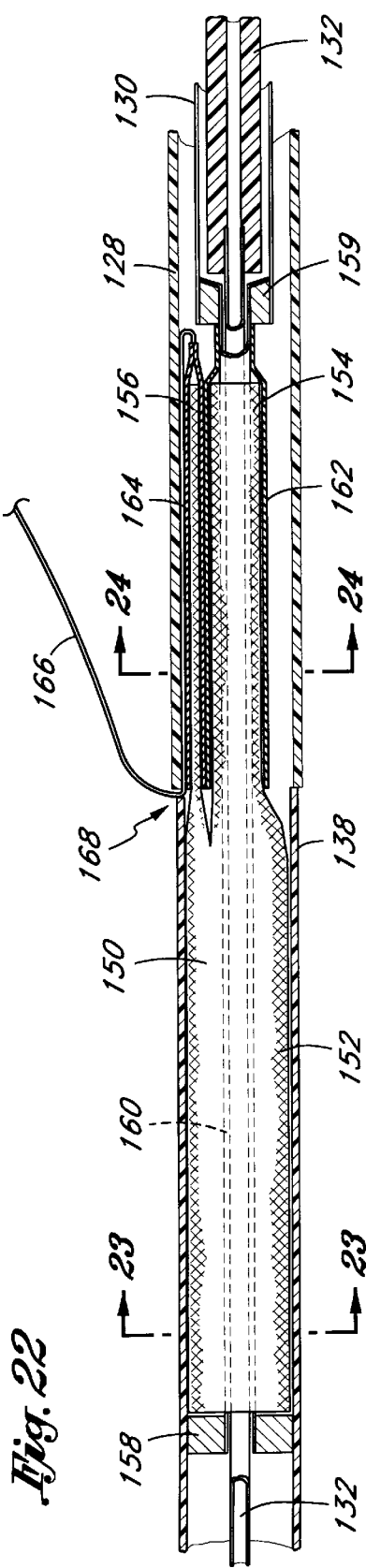
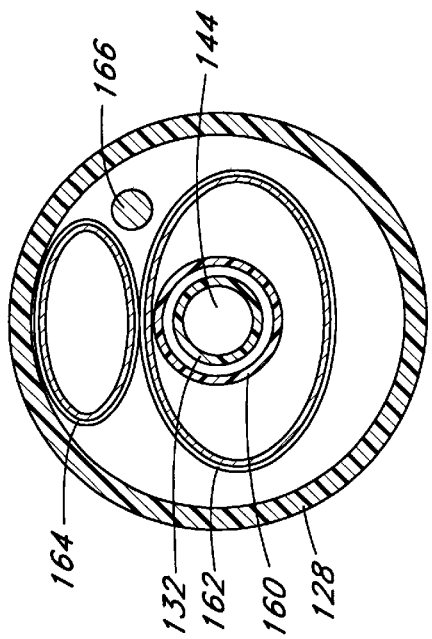
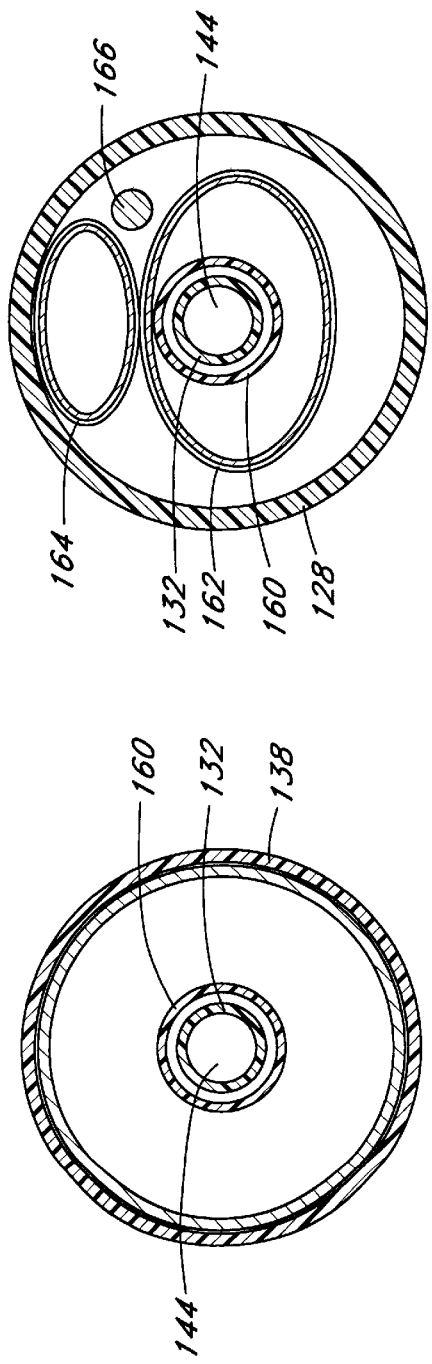

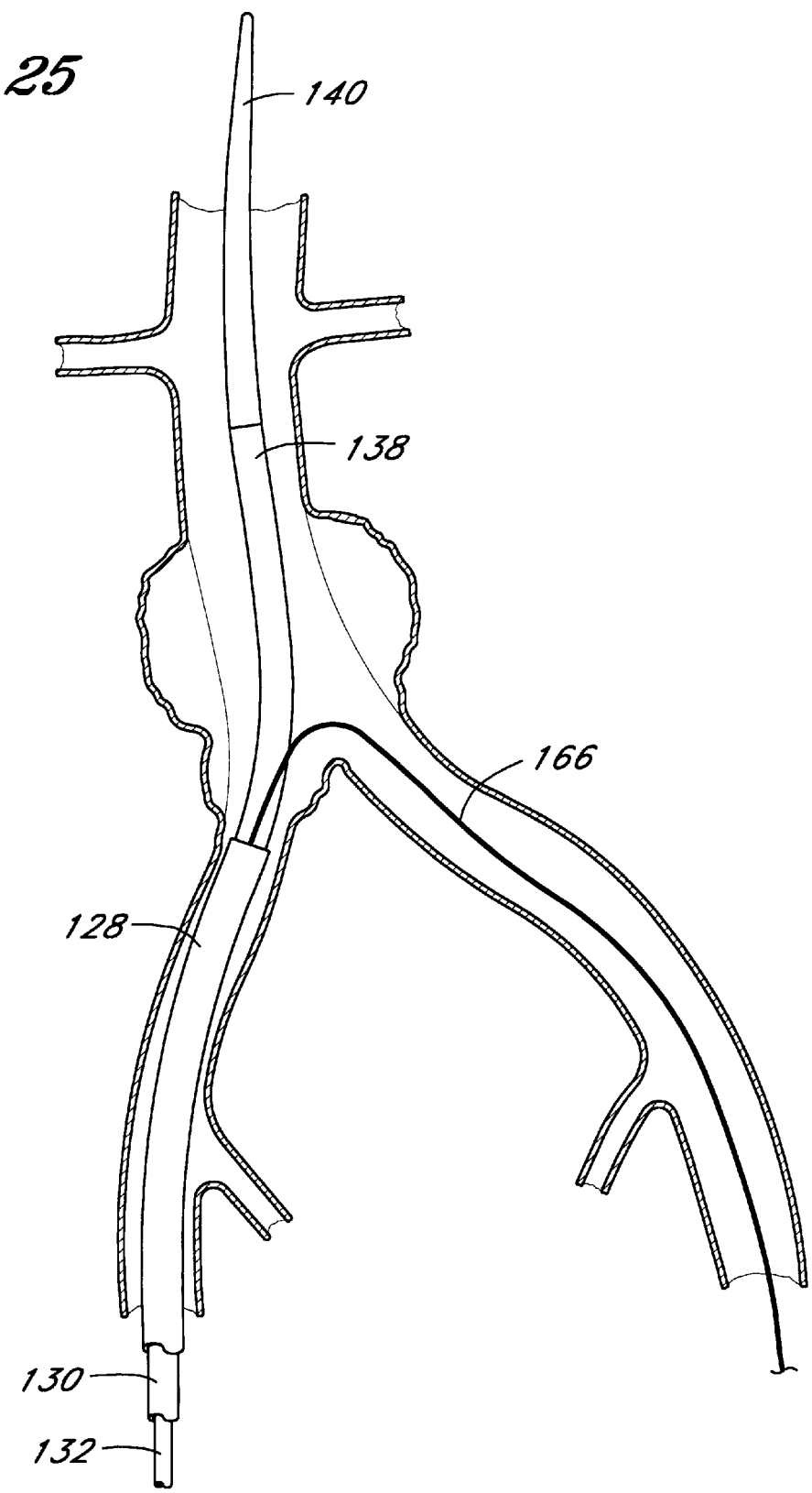

ENDOLUMINAL VASCULAR PROSTHESIS

BACKGROUND OF THE INVENTION

The present invention relates to endoluminal vascular prostheses, and, in one application, to self-expanding endoluminal vascular prostheses for use in the treatment of abdominal aortic aneurysms.

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, for example, below the kidneys. When left untreated, the aneurysm may eventually cause rupture of the sac with ensuing fatal hemorrhaging in a very short time. High mortality associated with the rupture led initially to transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of Polyester, Urethane, DACRON®, TEFLON®, or other suitable material.

To perform the surgical procedure requires exposure of the aorta through an abdominal incision which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off. The DACRON® tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still quite high. If the surgery is performed prior to the aneurysm rupturing, the mortality rate is typically slightly less than 10%. Conventional surgery performed after the rupture of the aneurysm is significantly higher, one study reporting a mortality rate of 66.5%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate include the extended recovery period associated with such surgery; difficulties in suturing the graft, or tube, to the aorta; the loss of the existing aorta wall and thrombosis to support and reinforce the graft; the unsuitability of the surgery for many patients having abdominal aortic aneurysms; and the problems associated with performing the surgery on an emergency basis after the aneurysm has ruptured. A patient can expect to spend from one to two weeks in the hospital after the surgery, a major portion of which is spent in the intensive care unit, and a convalescence period at home from two to three months, particularly if the patient has other illnesses such as heart, lung, liver, and/or kidney disease, in which case the hospital stay is also lengthened. Since the graft must be secured, or sutured, to the remaining portion of the aorta, it is many times difficult to perform the suturing step because the thrombosis present on the remaining portion of the aorta, and that remaining portion of the aorta wall may many times be friable, or easily crumbled.

Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such major surgery.

More recently, a significantly less invasive clinical approach to aneurysm repair, known as endovascular grafting, has been developed. Parodi, et al. provide one of the first clinical descriptions of this therapy. Parodi, J. C., et al., "Transfemoral Intraluminal Graft Implantation for Abdominal Aortic Aneurysms," 5 Annals of Vascular Surgery 491 (1991). Endovascular grafting involves the transluminal placement of a prosthetic arterial graft within the lumen of the artery.

In general, transluminally implantable prostheses adapted for use in the abdominal aorta comprise a tubular wire cage surrounded by a tubular PTFE or Dacron sleeve. Both balloon expandable and self expandable support structures have been proposed. Endovascular grafts adapted to treat both straight segment and bifurcation aneurysms have also been proposed.

Notwithstanding the foregoing, there remains a need for a structurally simple, easily deployable transluminally implantable endovascular prosthesis, with a support structure adaptable to span either a straight or bifurcated abdominal aortic aneurysm. Preferably, the tubular prosthesis can be self expanded at the site to treat the abdominal aortic aneurysm, and exhibits flexibility to accommodate nonlinear anatomies and normal anatomical movement.

SUMMARY OF THE INVENTION

There is provided in accordance with one aspect of the present invention, a moveable link for securing two portions of the wall of a tubular endovascular prosthesis. The link comprises a first wire portion having two side-by-side legs extending in a first direction and an apex thereon. A second wire portion is positioned adjacent the first wire portion. The first wire portion is wrapped around the second wire portion so that at least a portion of the apex faces in the first direction to at least partially entrap the second wire portion.

In accordance with another aspect of the present invention, there is provided an endoluminal prosthesis. The prosthesis comprises a tubular wire support having a proximal end, a distal end and a central lumen extending therethrough. The wire support comprises at least a first and a second axially adjacent tubular segments, joined by at least one folded link extending therebetween. The first and second segments and the link are preferably formed from a single length of wire.

Preferably, at least three folded links are provided between the first and second segments. The wire in each segment preferably comprises a series of proximal bends, a series of distal bends, creating a series of strut segments connecting the proximal bends and the distal bends to form a tubular segment wall. The folded link comprises a proximal or distal bend, together with a portion of two struts joined by the bend, extending through the loop formed by the other of the proximal and distal bends, to moveably link adjacent segments.

In accordance with a further aspect of the present invention, there is provided a method of making an endoluminal prosthesis. The method comprises the steps of providing a length of wire, and forming the wire into two or more zig-zag sections having proximal and distal apexes. The formed wire is rolled about an axis to produce two or more tubular elements positioned along the axis such that at least one proximal apex on one section axially overlaps with a distal apex on a second section. One of the proximal apex and distal apex is folded through the other of the proximal apex and the distal apex to produce a folded link. Preferably, the method further comprises the step of positioning a tubular polymeric sleeve concentrically on at least one of the tubular elements. In one embodiment, the tubular polymeric sleeve comprises PTFE.

In accordance with another aspect of the present invention, there is provided an endoluminal prosthesis. The prosthesis comprises an elongate flexible wire, formed into a plurality of axially adjacent tubular segments spaced along an axis, each tubular segment comprising a zig-zag section of the wire, having a plurality of proximal bends and distal bends. The wire continues between each adjacent tubular segment. At least two side-by-side wire segments joined by a first bend on a first tubular element extend through and interlock around a portion of a second tubular segment to provide a moveable link. The prosthesis is radially compressible into a first, reduced cross-section for implantation into a body lumen, and self expandable to a second, enlarged cross-sectional configuration at a treatment site in a body lumen.

Preferably, the prosthesis further comprises an outer tubular sleeve surrounding at least a portion of the prosthesis. Preferably, at least three segments are formed from the wire. The prosthesis has an expansion ratio of at least about 1:4, and an expanded diameter of at least about 20 mm to 30 mm in an unconstrained expansion.

Preferably, each axially adjacent pair of segments is characterized by an interface therebetween, wherein at least some of the proximal bends on one segment align with distal bends on the other segment to provide an opposing apex pair, and at least 30% of the apex pairs in a given interface are interlocked.

Further features and advantages of the present invention will become apparent to those of ordinary skill in the art in view of the disclosure herein, when considered together with the attached drawings and claims.

BRIEF DESCRIPTION OF THE DRAWINGS

FIG. 3 is a plan view of a formed wire useful for rolling about an axis into a multi-segment support structure in accordance with the present invention.

FIG. 4 is an enlarged detail view of a portion of the formed wire illustrated in FIG. 3.

FIG. 7 is an enlarged view of a folded link, taken along the lines 7—7 in FIG. 5.

FIG. 8 is a cross-sectional view taken along the line 8—8 in FIG. 7.

FIG. 13 is a schematic illustration of a straight segment delivery catheter in accordance with the present invention, positioned within an abdominal aortic aneurysm.

FIG. 14 is an illustration as in FIG. 13, with the straight segment endoluminal prosthesis partially deployed from the delivery catheter.

FIG. 17 is a schematic representation of a bifurcated vascular prosthesis in accordance with the present invention, positioned at the bifurcation between the abdominal aorta and the right and left common iliac arteries.

FIG. 18 is a cross-sectional view of the implanted graft taken along the lines 18—18 of FIG. 17.

FIG. 19 is an exploded view of the bifurcated vascular prosthesis in accordance with the present invention, showing a two-part self expandable wire support structure separated from an outer tubular sleeve.

FIG. 21 is side elevational cross-section of a bifurcation graft delivery catheter in accordance with the present invention.

FIG. 22 is an enlargement of the portion delineated by the line 22—22 in FIG. 21.

FIG. 23 is a cross-section taken along the line 23—23 in FIG. 22.

FIG. 24 is a cross-section taken along the line 24—24 in FIG. 22.

FIG. 25 is a schematic representation of a bifurcated graft deployment catheter of the present invention, positioned within the ipsilateral iliac and the aorta, with the contralateral guidewire positioned within the contralateral iliac.

DETAILED DESCRIPTION OF THE PREFERRED EMBODIMENT

Figure 1:
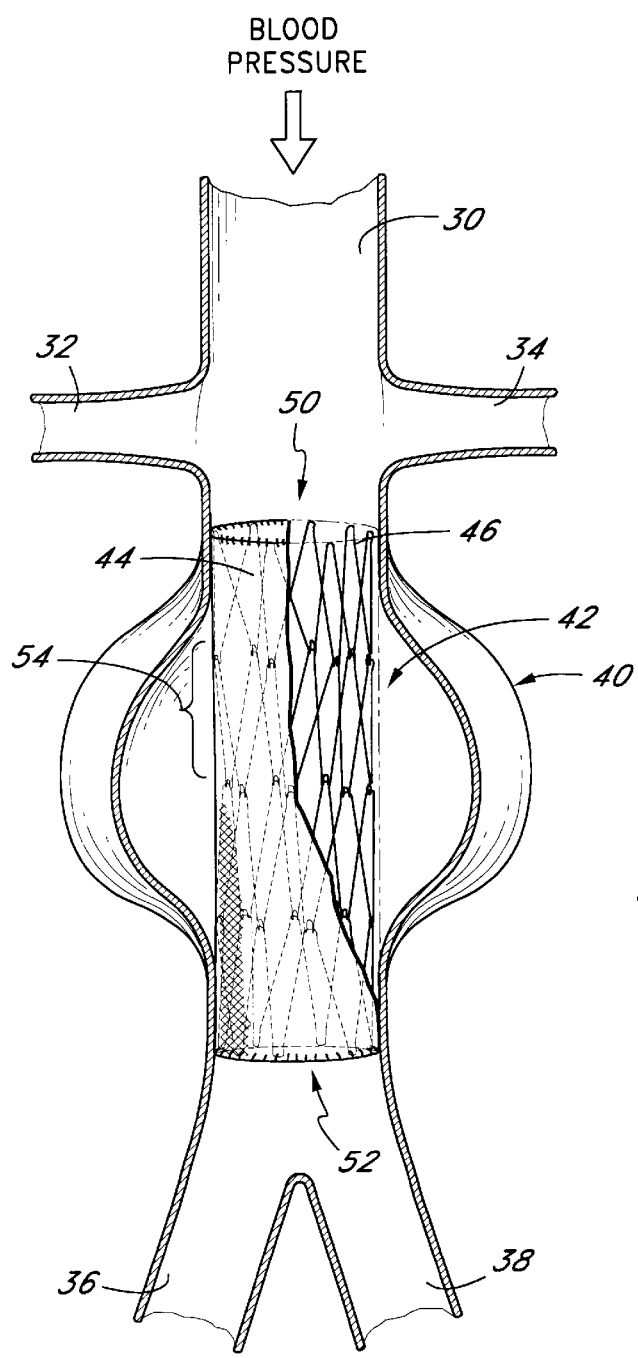
FIG. 1 is a schematic representation of a straight segment vascular prosthesis in accordance with the present invention, positioned within a symmetric abdominal aortic aneurysm.

Referring to FIG. 1, there is disclosed a schematic representation of the abdominal part of the aorta and its principal branches. In particular, the abdominal aorta 30 is characterized by a right renal artery 32 and left renal artery 34. The large terminal branches of the aorta are the right and left common iliac arteries 36 and 38. Additional vessels (e.g., second lumbar, testicular, inferior mesenteric, middle sacral) have been omitted for simplification. A generally symmetrical aneurysm 40 is illustrated in the infrarenal portion of the diseased aorta. An expanded straight segment endoluminal vascular prosthesis 42, in accordance with the present invention, is illustrated spanning the aneurysm 40.

The endoluminal vascular prosthesis 42 includes a polymeric sleeve 44 and a tubular wire support 46, which are illustrated in situ in FIG. 1. The sleeve 44 and wire support 46 are more readily visualized in the exploded view shown in FIG. 2. The endoluminal prosthesis 42 illustrated and described herein depicts an embodiment in which the polymeric sleeve 44 is situated concentrically outside of the tubular wire support 46. However, other embodiments may include a sleeve situated instead concentrically inside the wire support or on both of the inside and the outside of the wire support. Alternatively, the wire support may be embedded within a polymeric matrix which makes up the sleeve. Regardless of whether the sleeve 44 is inside or outside the wire support 46, the sleeve may be attached to the wire support by any of a variety of means, including laser bonding, adhesives, clips, sutures, dipping or spraying or others, depending upon the composition of the sleeve 44 and overall graft design.

The polymeric sleeve 44 may be formed from any of a variety of synthetic polymeric materials, or combinations thereof, including PTFE, PE, PET, Urethane, Dacron, nylon, polyester or woven textiles. Preferably, the sleeve material exhibits relatively low inherent elasticity, or low elasticity out to the intended enlarged diameter of the wire cage 46. The sleeve material preferably has a thin profile, such as no larger than about 0.002 inches to about 0.005 inches.

In a preferred embodiment of the invention, the material of sleeve 44 is sufficiently porous to permit ingrowth of endothelial cells, thereby providing more secure anchorage of the prosthesis and potentially reducing flow resistance, sheer forces, and leakage of blood around the prosthesis. Porosity in polymeric sleeve materials may be estimated by measuring water permeability as a function of hydrostatic pressure, which will preferably range from about 3 to 6 psi.

The porosity characteristics of the polymeric sleeve 44 may be either homogeneous throughout the axial length of the prosthesis 42, or may vary according to the axial position along the prosthesis 42. For example, referring to FIGS. 1 and 2, different physical properties will be called upon at different axial positions along the prosthesis 42 in use. At least a proximal portion 55 and a distal portion 59 of the prosthesis 42 will seat against the native vessel wall, proximally and distally of the aneurysm. In these proximal and distal portions, the prosthesis preferably encourages endothelial growth, or, at least, permits endothelial growth to infiltrate portions of the prosthesis in order to enhance anchoring and minimize leakage. A central portion 57 of the prosthesis spans the aneurysm, and anchoring is less of an issue. Instead, maximizing lumen diameter and minimizing blood flow through the prosthesis wall become primary objectives. Thus, in a central zone 57 of the prosthesis 42, the polymeric sleeve 44 may either be nonporous, or provided with pores of relatively lower porosity A multi-zoned prosthesis 42 may also be provided in accordance with the present invention by positioning a tubular sleeve 44 on a central portion 57 of the prosthesis, such that it spans the aneurysm to be treated, but leaving a proximal attachment zone 55 and a distal attachment zone 59 of the prosthesis 42 having exposed wires from the wire support 46. In this embodiment, the exposed wires 46 are positioned in contact with the vessel wall both proximally and distally of the aneurysm, such that the wire, over time, may become embedded in cell growth on the interior surface of the vessel wall.

Figure 2:
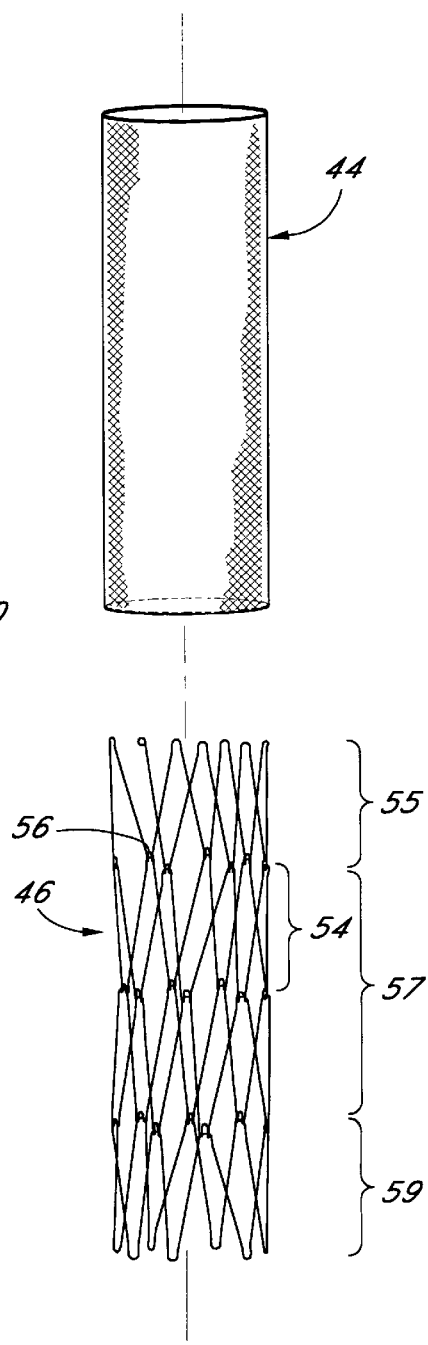
FIG. 2 is an exploded view of an endoluminal vascular prosthesis in accordance with the present invention, showing a self expandable wire support structure separated from an outer tubular sleeve.

In one embodiment of the prosthesis 42, the sleeve 44 and/or the wire support 46 is tapered, having a relatively larger expanded diameter at the proximal end 50 compared to the distal end 52. The tapered design may allow the prosthesis to conform better to the natural decreasing distal cross-section of the vessel, to reduce the risk of graft migration and potentially create better flow dynamics. The cage 46 can be provided with a proximal zone 55 and distal zone 59 that have a larger average expanded diameter than the central zone 57, as illustrated in FIG. 2. This configuration may desirably resist migration of the prosthesis within the vessel and reduce leakage around the ends of the prosthesis.

The tubular wire support 46 is preferably formed from a continuous single length of round or flattened wire. Alternatively, two or more wire lengths can be secured together to produce the wire support 46. The wire support 46 is preferably formed in a plurality of discrete tubular segments 54, connected together and oriented about a common axis. Each pair of adjacent segments 54 is connected by a connector 66 as will be discussed. The connectors 66 collectively produce a generally axially extending backbone which adds axial strength to the prosthesis 42. Adjacent segments can be connected both by the backbone, as well as the interlocking junction disclosed below. Additional structures, including circumferentially extending sutures, solder joints, and wire loops may also be used.

The segmented configuration of the tubular wire support 46 facilitates a great deal of flexibility. Each segment 54, though joined to adjacent segments, may be independently engineered to yield desired parameters. Each segment may range in axial length from about 0.3 to about 5 cm. Generally, the shorter their length the greater the radial strength. An endoluminal prosthesis may include from about 1 to about 50 segments, preferably from about 3 to about 10 segments. For example, while a short graft patch, in accordance with the invention, may comprise only 2 segments and span a total of 2 to 3 cm, a complete graft may comprise 4 or more segments and span the entire aortic aneurysm. In addition to the flexibility and other functional benefits available through employment of different length segments, further flexibility can be achieved through adjustments in the number, angle, or configuration of the wire bends associated with the tubular support.

In addition to having differing expanded diameters in different zones of the prosthesis 42, different zones can be provided with a different radial expansion force, such as ranging from about 0.2 lbs to about 0.8 lbs. In one embodiment, the proximal zone 55 is provided with a greater radial force than the central zone 57 and/or distal zone 59. The greater radial force can be provided in any of a variety of manners discussed elsewhere herein, such as through the use of an additional one or two or three or more proximal bends 60, distal bends 62 and wall sections 64 compared to a reference segment 54 in the central zone 57 or distal zone 59. Alternatively, additional spring force can be achieved in the proximal zone 55 through the use of the same number of proximal bends 60 as in the rest of the prosthesis, but with a heavier gauge wire.

The wire may be made from any of a variety of different alloys, such as elgiloy, nitinol or MP35N, or other alloys which include nickel, titanium, tantalum, or stainless steel, high Co—Cr alloys or other temperature sensitive materials. For example, an alloy comprising Ni 15%, Co 40%, Cr 20%, Mo 7% and balance Fe may be used. The tensile strength of suitable wire is generally above about 300 Ksi and often between about 300 and about 340 Ksi for many embodiments. In one embodiment, a Chromium-Nickel-Molybdenum alloy such as that marketed under the name Conichrom (Fort Wayne Metals, Indiana) has a tensile strength ranging from 300 to 320 K psi, elongation of 3.5–4.0%. The wire may be treated with a plasma coating and be provided with or without additional coatings such as PTFE, Teflon, Perlyne and drugs.

In addition to segment length and bend configuration, discussed above, another determinant of radial strength is wire gauge. The radial strength, measured at 50% of the collapsed profile, preferably ranges from about 0.2 lb to 0.8 lb, and generally from about 0.4 lb to about 0.5 lb. or more. Preferred wire diameters in accordance with the present invention range from about 0.004 inches to about 0.020 inches. More preferably, the wire diameters range from about 0.006 inches to about 0.018 inches. In general, the greater the wire diameter, the greater the radial strength for a given wire layout. Thus, the wire gauge can be varied depending upon the application of the finished graft, in combination with/or separate from variation in other design parameters (such as the number of struts, or proximal bends 60 and distal bends 62 per segment), as will be discussed. A wire diameter of approximately 0.018 inches may be useful in a graft having four segments each having 2.5 cm length per segment, each segment having six struts intended for use in the aorta, while a smaller diameter such as 0.006 inches might be useful for a 0.5 cm segment graft having 5 struts per segment intended for the iliac artery. The length of cage 42 could be as long as about 28 cm.

In one embodiment of the present invention, the wire diameter is tapered from the proximal to distal ends. Alternatively, the wire diameter may be tapered incrementally or stepped down, or stepped up, depending on differing radial strength requirements along the length of the graft for each particular clinical application. In one embodiment, intended for the abdominal aortic artery, the wire has a cross-section of about 0.018 inches in the proximal zone 55 and the wire tapers down to a diameter of about 0.006 inches in the distal zone 59 of the graft 42. End point dimensions and rates of taper can be varied widely, within the spirit of the present invention, depending upon the desired clinical performance.

Referring to FIG. 3, there is illustrated a plan view of a single formed wire used for rolling about a longitudinal axis to produce a four segment straight tubular wire support. The formed wire exhibits distinct segments, each corresponding to an individual tubular segment 54 in the tubular support (see FIGS. 1 and 2).

Each segment has a repeating pattern of proximal bends 60 connected to corresponding distal bends 62 by wall sections 64 which extend in a generally zig zag configuration when the segment 54 is radially expanded. Each segment 54 is connected to the adjacent segment 54 through a connector 66, except at the terminal ends of the graft. The connector 66 in the illustrated embodiment comprises two wall sections 64 which connect a proximal bend 60 on a first segment 54 with a distal bend 62 on a second, adjacent segment 54. The connector 66 may additionally be provided with a connector bend 68, which may be used to impart increased radial strength to the graft and/or provide a tic site for a circumferentially extending suture.

Referring to FIG. 4, there is shown an enlarged view of the wire support illustrating a connector 66 portion between adjacent segments 54. In the embodiment shown in FIG. 4, a proximal bend 60 comprises about a 180 degree arc, having a radial diameter of (w) (Ranging from 0.070 to 0.009 inches), depending on wire diameter followed by a relatively short length of parallel wire spanning an axial distance of d1. The parallel wires thereafter diverge outwardly from one another and form the strut sections 64, or the proximal half of a connector 66. At the distal end of the strut sections 64, the wire forms a distal bend 62, preferably having identical characteristics as the proximal bend 60, except being concave in the opposite direction. The axial direction component of the distance between the apices of the corresponding proximal and distal bends 60, 62 on a given strut section 64 is referred to as (d) and represents the axial length of that segment. The total expanded angle defined by the bend 60 and the divergent strut sections 64 is represented by α. Upon compression to a collapsed state, such as when the graft is within the deployment catheter, the angle α is reduced to α'. In the expanded configuration, α is generally within the range of from about 35° to about 45° for a six apex section having an axial length of about 1.5 cm or 2 cm and a diameter of about 25 mm or 28 mm. The expanded circumferential distance between any two adjacent distal bends 62 (or proximal bends 60) is defined as (s).

In general, the diameter W of each proximal bend 60 or distal bend 62 is within the range of from about 0.009 inches to about 0.070 inches depending upon the wire diameter. Diameter W is preferably as small as possible for a given wire diameter and wire characteristics. As will be appreciated by those of skill in the art, as the distance W is reduced to approach two times the cross-section of the wire, the bend 60 or 62 will exceed the elastic limit of the wire, and radial strength of the finished segment will be lost. Determination of a minimum value for W, in the context of a particular wire diameter and wire material, can be readily determined through routine experimentation by those of skill in the art.

As will be appreciated from FIGS. 3 and 4, the sum of the distances (s) in a plane transverse to the longitudinal axis of the finished graft will correspond to the circumference of the finished graft cage in that plane. For a given circumference, the number of proximal bends 60 or distal bends 62 is directly related to the distance (s) in the corresponding plane. Preferably, the finished graft in any single transverse plane will have from about 3 to about 10 (s) dimensions, preferably from about 4 to about 8 (s) dimensions and, more preferably, about 5 or 6 (s) dimensions for an aortic application. Each (s) dimension corresponds to the distance between any two adjacent bends 60–60 or 62–62 as will be apparent from the discussion herein. Each segment 54 can thus be visualized as a series of triangles extending circumferentially around the axis of the graft, defined by a proximal bend 60 and two distal bends 62 or the reverse.

In one embodiment of the type illustrated in FIG. 4, w is about 2.0 mm±1 mm for a 0.018 inch wire diameter. D1 is about 3 mm±1 mm, and d is about 20 mm±1 mm. Specific dimensions for all of the foregoing variables can be varied considerably, depending upon the desired wire configuration, in view of the disclosure herein.

Figure 5:
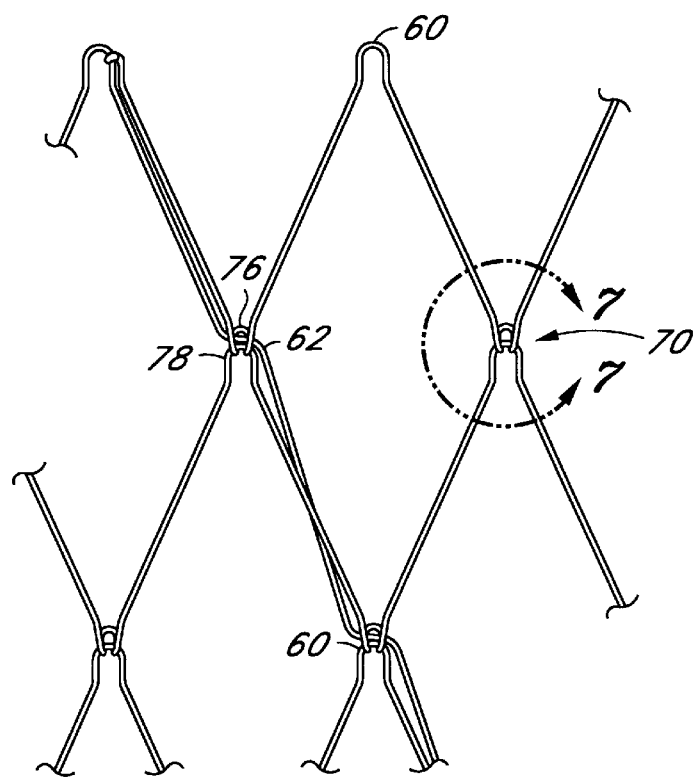
FIG. 5 is a schematic view of a portion of a wire cage wall, illustrating folded link connections between adjacent apexes.
Figure 6:
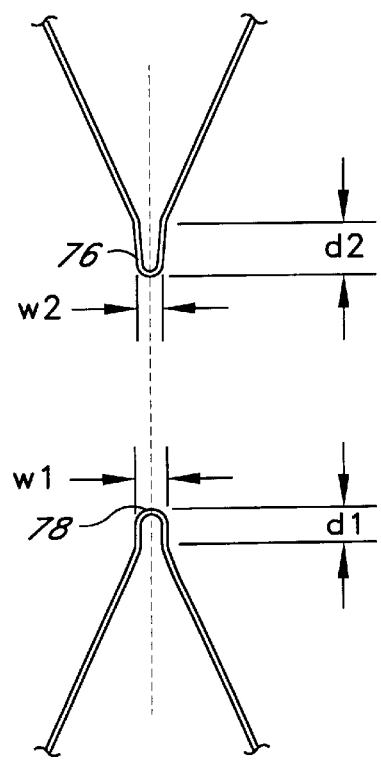
FIG. 6 is an exploded view of two opposing apexes dimensioned for one embodiment of the folded link connection of the present invention.

Referring to FIGS. 5 and 6, one or more apexes 76 is provided with an elongated axial length d2, which permits the apex 76 to be wrapped around a corresponding portion 78 such as an apex of the adjacent segment to provide an interlocking link 70 between two axially adjacent cage segments. In one embodiment of the link 70 produced by the opposing apexes 76 and 78 of FIG. 6, utilizing wire having a diameter from 0.012" to 0.018", d1 is generally within the range of from about 1 mm to about 4 mm and d2 is within the range of from about 5 mm to about 9 mm. In general, a longer d2 dimension permits accommodation for greater axial travel of apex 78 with respect to 76, as will be discussed, thereby permitting greater lateral flexibility of the graft. W1 is within the range of from about 3 mm to about 5 mm, and W2 is sufficiently less than W1 that the apex 76 can fit within the apex 78. Any of a wide variety of specific apex configurations and dimensions can be utilized, as will be apparent to those of skill in the art in view of the disclosure herein. Regardless of the specific dimensions, the end of the apex 76 is advanced through the apex 78, and folded back upon its self to hook the apex 78 therein to provide a link 70 in accordance with the present invention.

Figure 10:
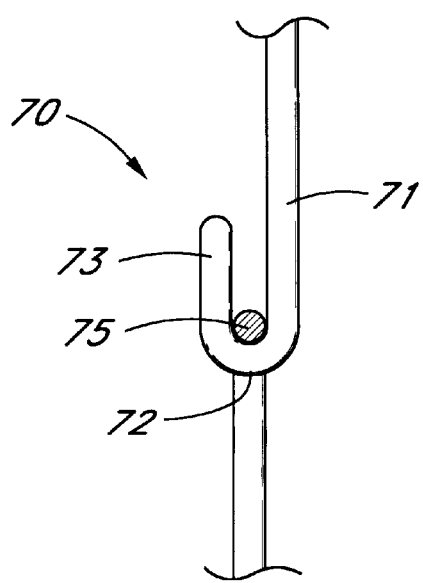
FIG. 10 is a cross-section taken along the line 10—10 in FIG. 9.
Figure 11:
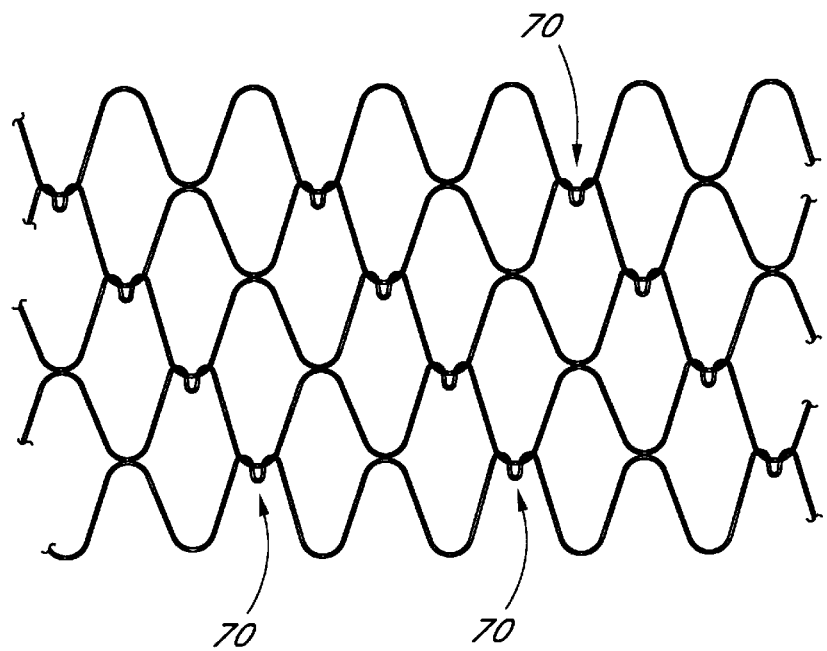
FIG. 11 is a schematic view of a portion of a wall of a graft, laid out flat, illustrating an alternating folded link pattern.

The resulting link 70 (see FIGS. 7 and 8) comprises a wall portion 71 extending in a first direction, substantially parallel to the axis of the graft, and a transverse portion 72 extending transverse to the axis of the graft. A return portion 73 extends generally in the opposite direction from the wall portion 71 to create a generally "U" shaped hook. In certain embodiments, a closing portion 74 is also provided, to minimize the risk of excessive axial compression of the wire cage. The forgoing structure produces a functionally closed aperture 77, which receives the interlocking section 75 of the adjacent graft segment. Alternatively, see FIG. 10.

In general, the aperture 77 preferably has a width (as viewed in FIG. 8) in the radial graft direction of substantially equal to the radial direction dimension of the interlocking section 75. In this embodiment, the interlocking section 75, as well as the locking portion 71 and return portion 73 can be flattened in the radial direction, to minimize the transverse cross-section of the link 70. In the axial direction, the aperture 77 is preferably greater than the axial direction dimension of the interlocking section 75, to accommodate some axial movement of each adjoining tubular segment of the graft. The axial length of the aperture 77 is at least about 2 times, and preferably at least about 3 or 4 times the cross-section of the interlocking section 75. The optimum axial length of the aperture 77 can be determined through routine experimentation by one of skill in the art in view of the intended clinical performance, taking into account the number of links 70 per transverse plane as well as the desired curvature of the finished graft.

Figure 6A:
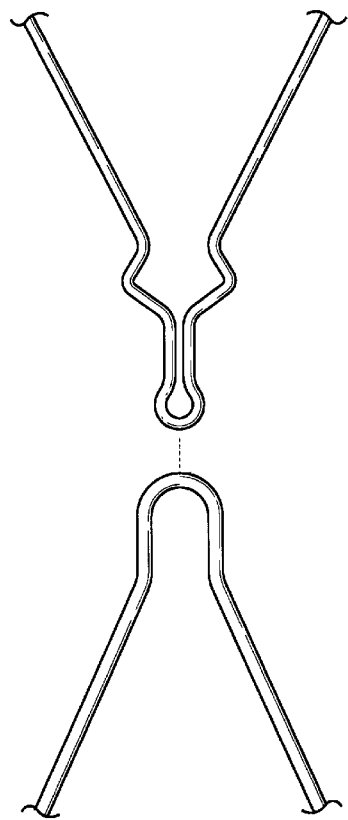
FIGS. 6A, 7A, 8A, 7B, 8B, 7C, and 7D illustrate alternate embodiments of a folded link constructed from an opposing apex pair.
Figure 7A:
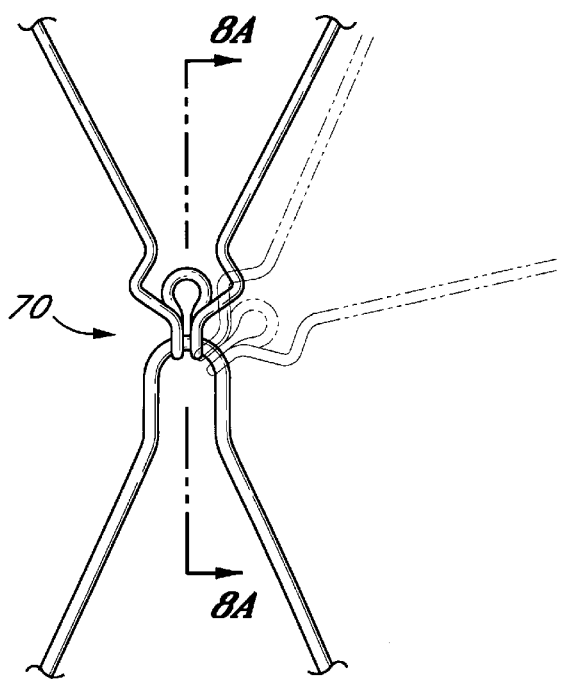
Figure 8A:
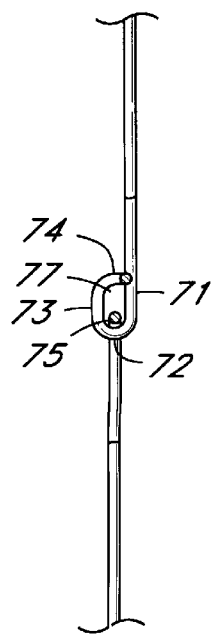

FIGS. 6A, 7A and 8A illustrate an alternate configuration for the moveable link 70. With this configuration, the radial expansion force will be higher.

Figure 7B:
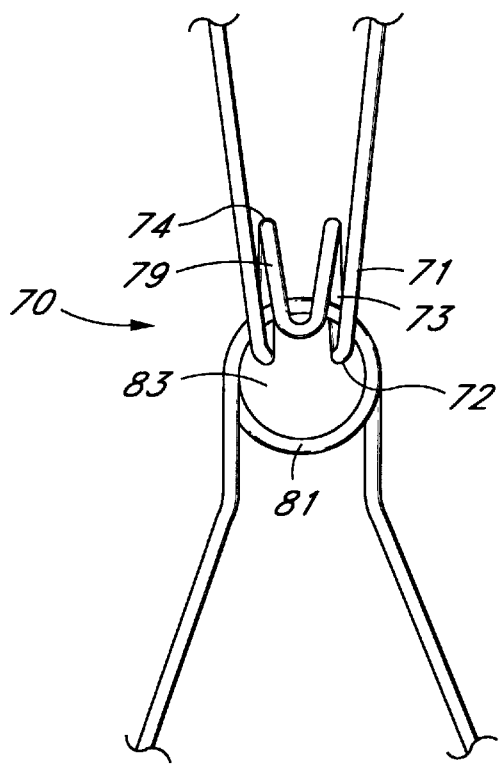
Figure 8B:
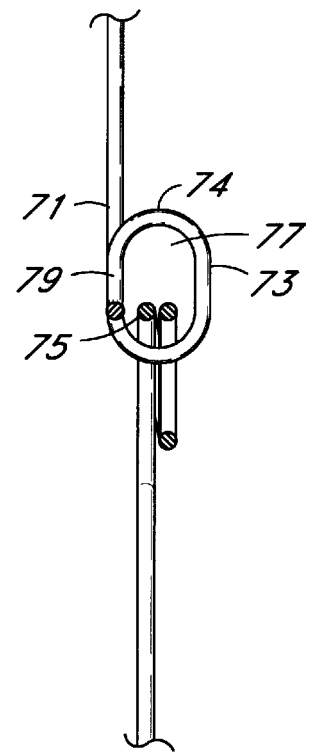
Figure 7C:
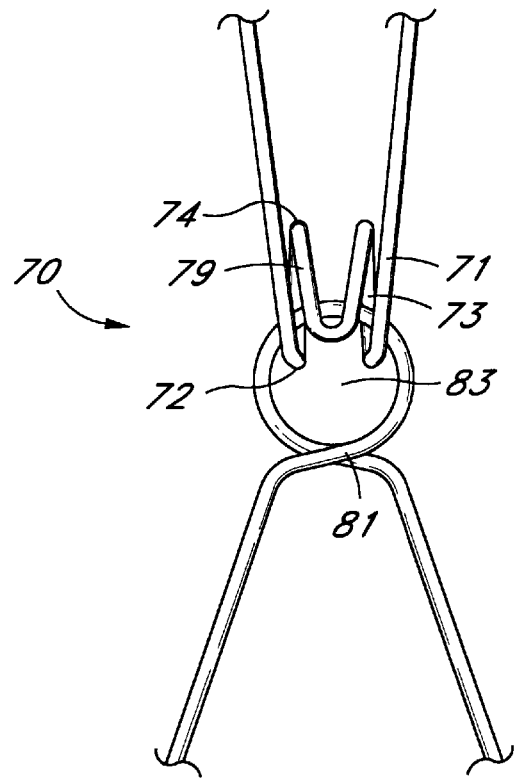
Figure 7D:
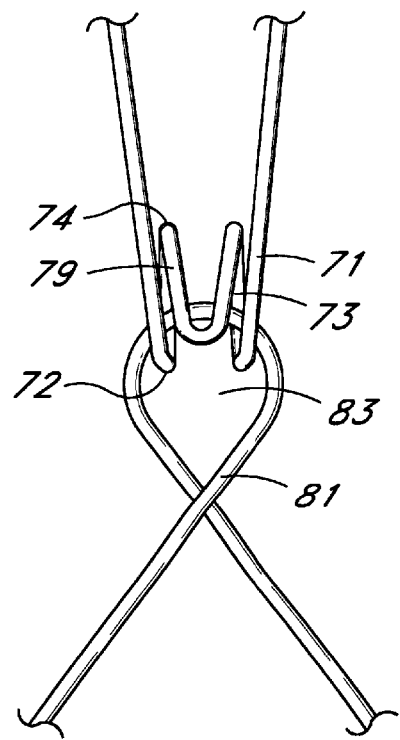

FIGS. 7B and 8B illustrate another alternate configuration. This linkage has a better resistance to axial compression and disengagement. Referring to FIGS. 7B and 8B, the apex extends beyond closing portion 74 and into an axial portion 79 which extends generally parallel to the longitudinal axis of the graft. Provision of an axial extension 79 provides a more secure enclosure for the aperture 77 as will be apparent to those of skill in the art. The embodiments of FIGS. 7B and 8B also illustrate an enclosed aperture 83 on the opposing apex. The aperture 83 is formed by wrapping the apex in at least one complete revolution so that a generally circumferentially extending portion 81 is provided. Circumferential portion 81 provides a stop, to limit axial compressibility of the graft. The closed aperture 83 can be formed by winding the wire of the apex about a mandrel either in the direction illustrated in FIG. 7B, or the direction illustrated in FIG. 7C. The embodiment of FIG. 7C advantageously provided only a single wire thickness through the aperture 77, thereby minimizing the wall thickness of the graft. This is accomplished by moving the crossover point outside of the aperture 77, as will be apparent from FIG. 7C.

The link 70 in accordance with the present invention is preferably formed integrally with the wire which forms the cage of the endovascular prosthesis. Alternatively, link 70 may be constructed from a separate material which is secured to the wire cage such as by soldering, suture, wrapping or the like.

Figure 9:
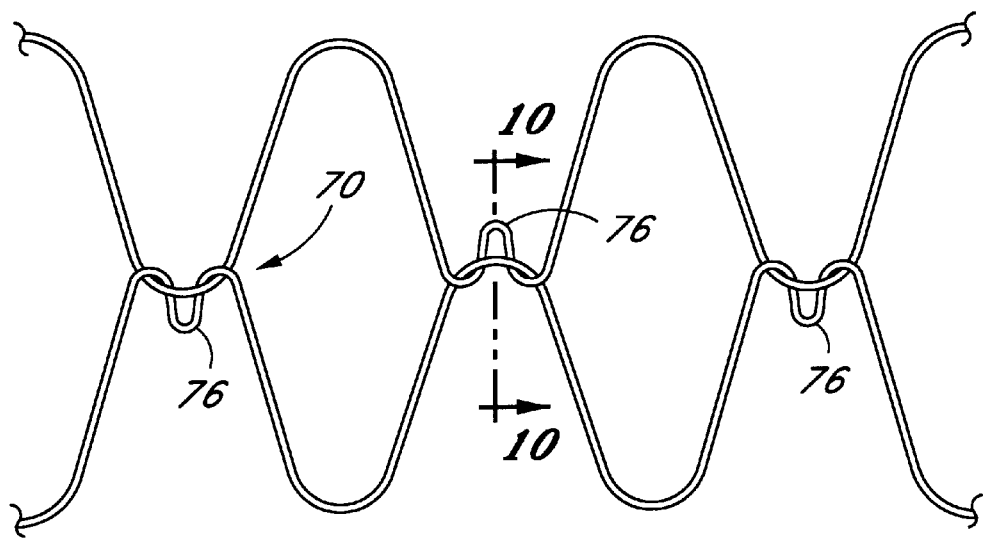
FIG. 9 is a partial view of a junction between two adjacent tubular segments, illustrating oppositely oriented folded links in accordance with the present invention.

The axial direction of the link 70 may also be varied, depending upon the desired performance characteristics of the graft. For example, the distal tips 76 of each link 70 may all face the same direction, such as proximal or distal with respect to the graft. See, for example, FIG. 5. Alternatively, one or more links in a given transverse plane of apexes may face in a proximal direction, and one or more links in the same transverse plane may face in the opposite direction. See, for example, FIG. 9.

Regardless of the axial orientation of the link 70, at least one and preferably at least two links 70 are provided per transverse plane separating adjacent graft segments. In an embodiment having six apexes per transverse plane, preferably at least two or three and in one embodiment all six opposing apex pairs are provided with a link 70. See FIG. 5.

The distribution of the interlocking link 70 throughout the wire cage can thus vary widely, depending upon the desired performance characteristics. For example, each opposing apex pair between adjacent tubular segments can be provided with a link 70. See FIG. 5. Alternatively, interlocking links 70 may be spaced circumferentially apart around the graft wall such as by positioning them at every second or third opposing apex pair.

Figure 12:
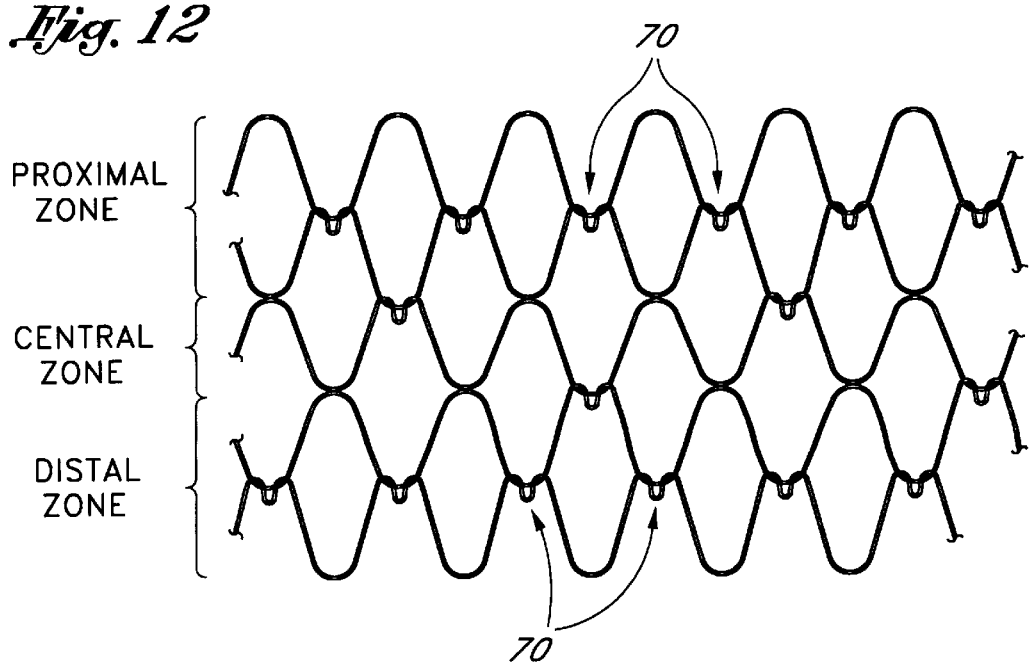
FIG. 12 is a wall pattern as in FIG. 11, illustrating a multi-zone folded link pattern.

The distribution of the links 70 may also be varied along the axial length of the graft. For example, a first zone at a proximal end of the graft and a second zone at a distal end of the graft may be provided with a relatively larger number of links 70 than a third zone in the central portion of the graft. In one embodiment, the transverse apex plane between the first and second tubular segments at the proximal end of the graft may be provided with a link 70 at each opposing apex pair. This has been determined by the present inventors to increase the radial strength of the graft, which may be desirable at the proximal (superior) end of the graft and possibly also at the distal end of the graft where resistance to leakage is an issue. A relatively lesser radial strength may be necessary in the central portion of the graft, where maintaining patency of the lumen is the primary concern. For this reason, relatively fewer links 70 may be utilized in a central zone, in an effort to simply graft design as well as reduce collapse profile of the graft. See FIG. 12.

In one straight segment graft, having four graft segments, three transverse apex planes are provided. In the proximal apex plane, each opposing pair of apexes is provided with a link 70. In the central transverse apex plane, three of the six apex pairs are provided with a links 70, spaced apart at approximately 120°. Substantially equal circumferential spacing of the link 70 is preferred, to provide relatively uniform resistance to bending regardless of graft position. The distal transverse apex plane may also be provided with a link 70 at each opposing apex pair.

The foregoing interlocking link 70 in accordance with the present invention can be readily adapted to both the straight segment grafts as discussed above, as well as to the bifurcated grafts discussed below.

The interlocking link 70 can be utilized to connect any of a number of independent graft segments in axial alignment to produce either a straight segment or a bifurcation graft. The interlocking link 70 may be utilized as the sole means of securing adjacent segments to each other, or may be supplemented by additional attachment structures such as metal loops, sutures, welds and others which are well understood in the art.

Figure 12A:
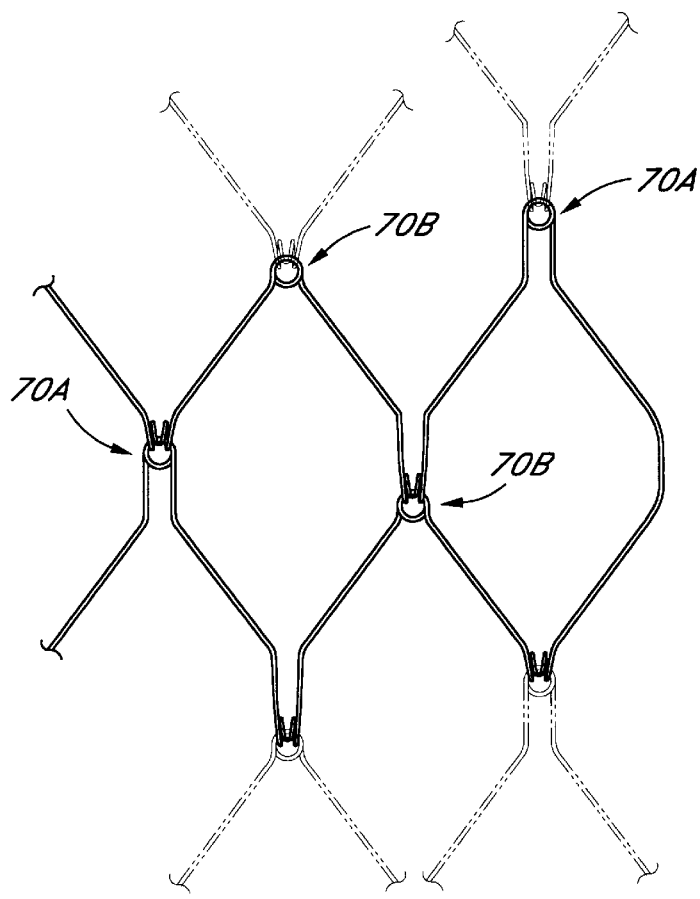
FIGS. 12A through 12C illustrate an alternate wall pattern, which permits axially staggered links between adjacent graft segments.
Figure 12B:
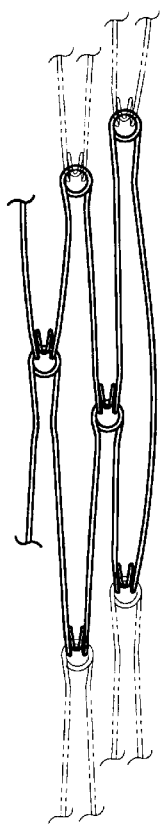
Figure 12C:
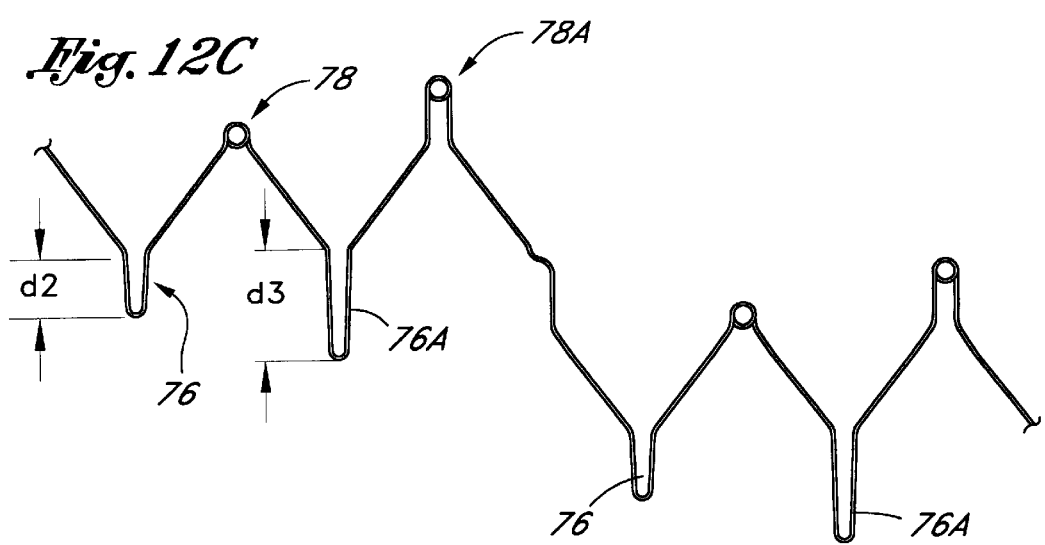

Referring to FIGS. 12A through 12C there is illustrated a further wire layout which allows a smaller collapsed profile for the vascular graft. In general, the embodiment of FIGS. 12A through 12C permits a series of links 70A and 70B to be staggered axially from one another as seen in FIGS. 12A and 12B. In this manner, adjacent links 70 do not lie in the same transverse plane, and permit a tighter nesting of the collapsed wire cage. Preferably, between each adjoining graft segment, at least a first group of links 70A is offset axially from a second group of links 70B. In a six apex graft, having a link 70 at each apex, for example, a first group of every other apex 70A may be positioned slightly proximally of a second group of every other apex 70B. Referring to FIG. 12C, this may be accomplished by extending an apex 76A by a d3 distance which is at least about 1.2 times and as large as 1.5 times or 2 times or more the distance d2. The corresponding apexes 78 and 78A are similarly staggered axially, to produce the staggered interface between adjacent graft segments illustrated in FIG. 12A. Although a loop apex is illustrated in FIG. 12C as apex 78, any of the alternate apexes illustrated herein can be utilized in the staggered apex embodiment of the invention. The zig-zag pattern produced by axially offset links 70A and 70B can reside in a pair of parallel transverse planes extending generally between adjacent segments of the graft. Alternatively, the zig-zag relationship between adjacent links 70A and 70B can spiral around the circumference of a graft in a helical pattern, as will be understood by those of skill in the art in view of the disclosure herein. The precise axial offset between adjacent staggered links 70A and 70B can be optimized by one of ordinary skill in the art through routine experimentation, taking into account the desired physical properties and collapsed profile of the graft.

Referring to FIGS. 13 and 14, a straight segment deployment device and method in accordance with a preferred embodiment of the present invention are illustrated. A delivery catheter 80, having a dilator tip 82, is advanced along guidewire 84 until the (anatomically) proximal end 50 of the collapsed endoluminal vascular prosthesis 88 is positioned between the renal arteries 32 and 34 and the aneurysm 40. The collapsed prosthesis in accordance with the present invention has a diameter in the range of about 2 to about 10 mm. Generally, the diameter of the collapsed prosthesis is in the range of about 3 to 6 mm (12 to 18 French). Preferably, the delivery catheter including the prosthesis will be 16 F, or 15 F or 14 F or smaller.

The prosthesis 88 is maintained in its collapsed configuration by the restraining walls of the tubular delivery catheter 80, such that removal of this restraint would allow the prosthesis to self expand. Radiopaque marker material may be incorporated into the delivery catheter 80, and/or the prosthesis 88, at least at both the proximal and distal ends, to facilitate monitoring of prosthesis position. The dilator tip 82 is bonded to an internal catheter core 92, as illustrated in FIG. 14, so that the internal catheter core 92 and the partially expanded prosthesis 88 are revealed as the outer sheath of the delivery catheter 80 is retracted.

As the outer sheath is retracted, the collapsed prosthesis 88 remains substantially fixed axially relative to the internal catheter core 92 and consequently, self-expands at a predetermined vascular site as illustrated in FIG. 14. Continued retraction of the outer sheath results in complete deployment of the graft. After deployment, the expanded endoluminal vascular prosthesis 88 has radially self-expanded to a diameter anywhere in the range of about 20 to 40 mm, corresponding to expansion ratios of about 1:2 to 1:20. In a preferred embodiment, the expansion ratios range from about 1:4 to 1:8, more preferably from about 1:4 to 1:6.

In addition to, or in place of, the outer sheath described above, the prosthesis 88 may be maintained in its collapsed configuration by a restraining lace, which may be woven through the prosthesis or wrapped around the outside of the prosthesis in the collapsed reduced diameter. Following placement of the prosthesis at the treatment site, the lace can be proximally retracted from the prosthesis thereby releasing it to self expand at the treatment site. The lace may comprise any of a variety of materials, such as sutures, strips of PTFE, FEP, polyester fiber, and others as will be apparent to those of skill in the art in view of the disclosure herein. The restraining lace may extend proximally through a lumen in the delivery catheter or outside of the catheter to a proximal control. The control may be a pull tab or ring, rotatable reel, slider switch or other structure for permitting proximal retraction of the lace. The lace may extend continuously throughout the length of the catheter, or may be joined to another axially moveable element such as a pull wire.

In general, the expanded diameter of the graft in accordance with the present invention can be any diameter useful for the intended lumen or hollow organ in which the graft is to be deployed. For most arterial vascular applications, the expanded size will be within the range of from about 10 to about 40 mm. Abdominal aortic applications will generally require a graft having an expanded diameter within the range of from about 20 to about 28 mm, and, for example, a graft on the order of about 45 mm may be useful in the thoracic artery. The foregoing dimensions refer to the expanded size of the graft in an unconstrained configuration, such as on the table. In general, the graft will be positioned within an artery having a slightly smaller interior cross-section than the expanded size of the graft. This enables the graft to maintain a slight positive pressure against the wall of the artery, to assist in retention of the graft during the period of time prior to endothelialization of the polymeric sleeve 44.

The radial force exerted by the proximal segment 94 of the prosthesis against the walls of the aorta 30 provides a seal against the leakage of blood around the vascular prosthesis and tends to prevent axial migration of the deployed prosthesis. As discussed above, this radial force can be modified as required through manipulation of various design parameters, including the axial length of the segment and the bend configurations. In another embodiment of the present invention, radial tension can be enhanced at the proximal, upstream end by increasing the the wire gauge in the proximal zone. Wire diameter may range from about 0.001 to 0.01 inches in the distal region to a range of from about 0.01 to 0.03 inches in the proximal region.

An alternative embodiment of the wire layout which would cause the radial tension to progressively decrease from the proximal segments to the distal segments, involves a progressive or step-wise decrease in the wire gauge throughout the entire wire support, from about 0.01 to 0.03 inches at the proximal end to about 0.002 to 0.01 inches at the distal end. Such an embodiment, may be used to create a tapered prosthesis. Alternatively, the wire gauge may be thicker at both the proximal and distal ends, in order to insure greater radial tension and thus, sealing capacity. Thus, for instance, the wire gauge in the proximal and distal segments may about 0.01 to 0.03 inches, whereas the intervening segments may be constructed of thinner wire, in the range of about 0.001 to 0.01 inches.

Figure 15:
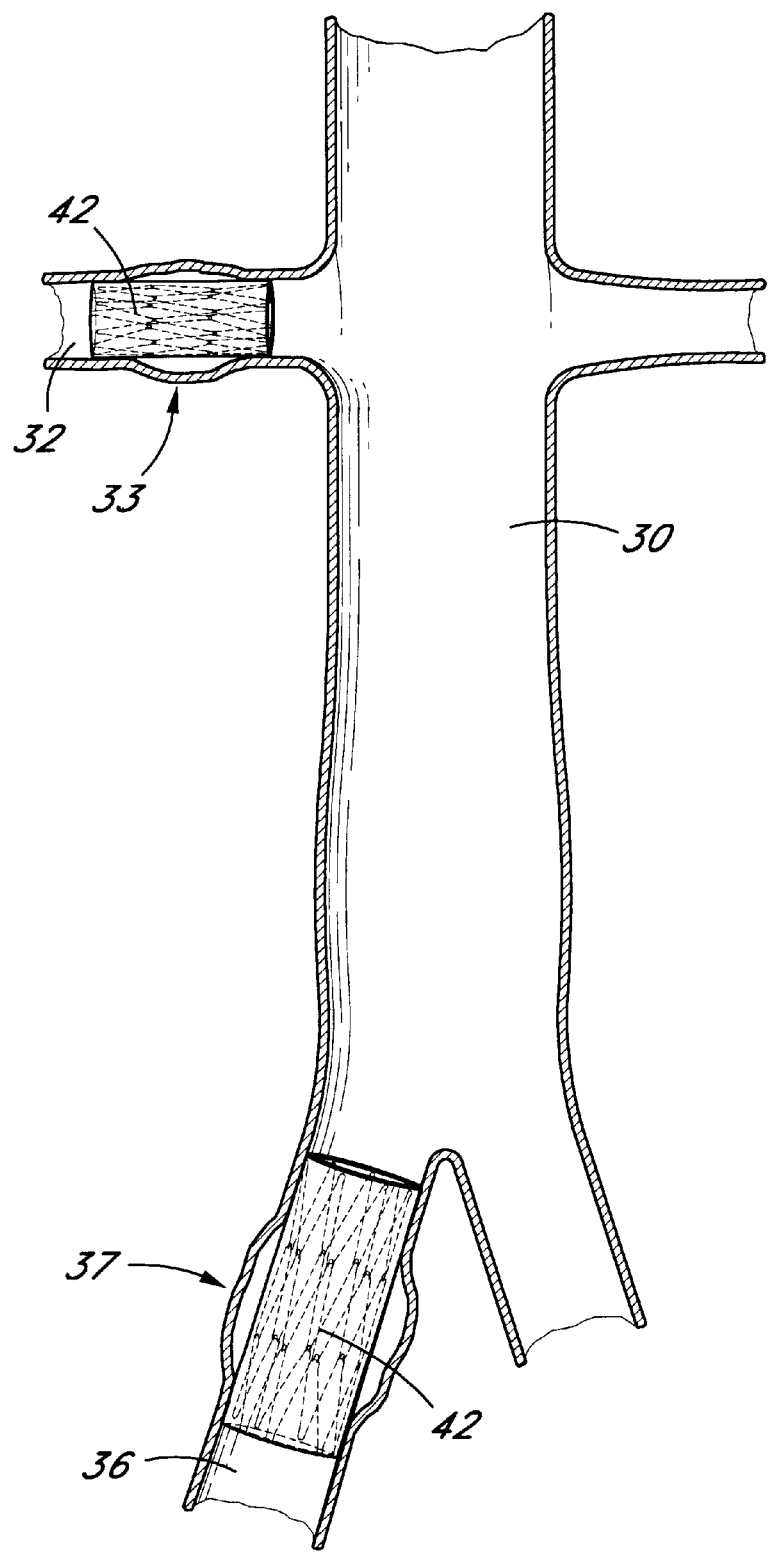
FIG. 15 is a schematic representation of the abdominal aortic anatomy, with an endoluminal vascular prostheses of the present invention positioned within each of the right renal artery and the right common iliac.

Referring to FIG. 15, there is illustrated two alternative deployment sites for the endoluminal vascular prosthesis 42 of the present invention. For example, an aneurysm 33 is illustrated in the right renal artery 32. An expanded endoluminal vascular prosthesis 42, in accordance with the present invention, is illustrated spanning that aneurysm 33. Similarly, an aneurysm 37 of the right common iliac 36 is shown, with a prosthesis 42 deployed to span the iliac aneurysm 37.

Figure 16:
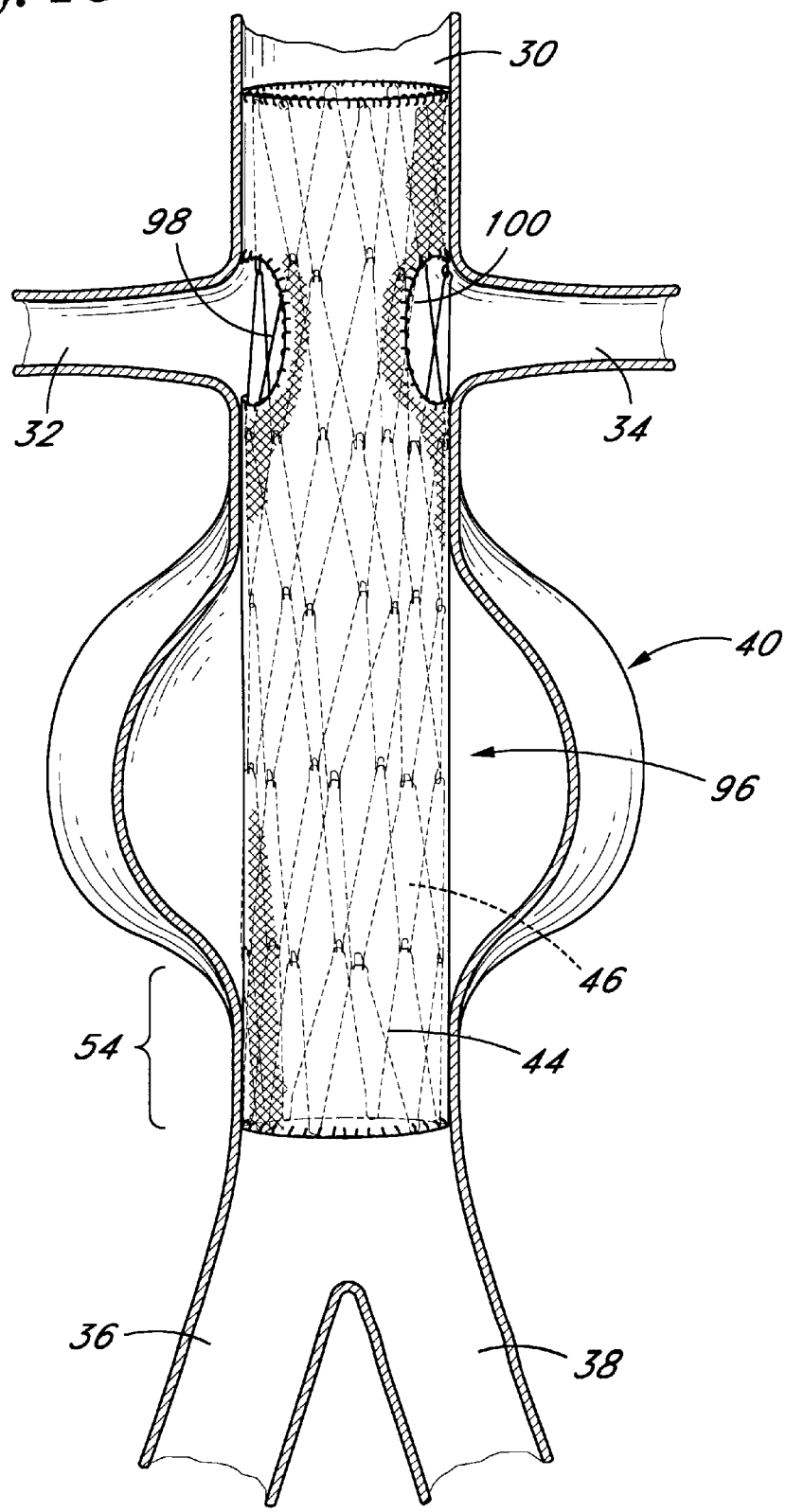
FIG. 16 is a schematic representation of a straight segment graft in accordance with a further embodiment of the present invention, with side openings to permit renal perfusion.

Referring to FIG. 16, there is illustrated a modified embodiment of the endovascular prosthesis 96 in accordance with the present invention. In the embodiment illustrated in FIG. 16, the endovascular prosthesis 96 is provided with a wire cage 46 having six axially aligned segments 54. As with the previous embodiments, however, the endovascular prosthesis 96 may be provided with anywhere from about 2 to about 10 or more axially spaced or adjacent segments 54, depending upon the clinical performance objectives of the particular embodiment.

The wire support 46 is provided with a tubular polymeric sleeve 44 as has been discussed. In the present embodiment, however, one or more lateral perfusion ports or openings are provided in the polymeric sleeve 44, such as a right renal artery perfusion port 98 and a left renal artery perfusion port 100 as illustrated.

Perfusion ports in the polymeric sleeve 44 may be desirable in embodiments of the endovascular prosthesis 96 in a variety of clinical contexts. For example, although FIGS. 1 and 16 illustrate a generally symmetrical aneurysm 40 positioned within a linear infrarenal portion of the abdominal aorta, spaced axially apart both from bilaterally symmetrical right and left renal arteries and bilaterally symmetrical right and left common iliacs, both the position and symmetry of the aneurysm 40 as well as the layout of the abdominal aortic architecture may differ significantly from patient to patient. As a consequence, the endovascular prosthesis 96 may need to extend across one or both of the renal arteries in order to adequately anchor the endovascular prosthesis 96 and/or span the aneurysm 40. The provision of one or more lateral perfusion ports or zones enables the endovascular prosthesis 96 to span the renal arteries while permitting perfusion therethrough, thereby preventing "stent jailing" of the renals. Lateral perfusion through the endovascular prosthesis 96 may also be provided, if desired, for a variety of other arteries including the second lumbar, testicular, inferior mesenteric, middle sacral, and alike as will be well understood to those of skill in the art.

The endovascular prosthesis 96 is preferably provided with at least one, and preferably two or more radiopaque markers, to facilitate proper positioning of the prosthesis 96 within the artery. In an embodiment having perfusion ports 98 and 100 such as in the illustrated design, the prosthesis 96 should be properly aligned both axially and rotationally, thereby requiring the ability to visualize both the axial and rotational position of the device. Alternatively, provided that the delivery catheter design exhibits sufficient torque transmission, the rotational orientation of the graft may be coordinated with an indexed marker on the proximal end of the catheter, so that the catheter may be rotated and determined by an external indicium of rotational orientation to be appropriately aligned with the right and left renal arteries.

In an alternative embodiment, the polymeric sleeve 44 extends across the aneurysm 40, but terminates in the infrarenal zone. In this embodiment, a proximal zone 55 on the prosthesis 96 comprises a wire cage 46 but no polymeric sleeve 44. In this embodiment, the prosthesis 96 still accomplishes the anchoring function across the renal arteries, yet does not materially interfere with renal perfusion. Thus, the polymeric sleeve 44 may cover anywhere from about 50% to about 100% of the axial length of the prosthesis 96 depending upon the desired length of uncovered wire cage 46 such as for anchoring and/or lateral perfusion purposes. In particular embodiments, the polymeric sleeve 44 may cover within the range of from about 70% to about 80%, and, in one four segment embodiment having a single exposed segment, 75%, of the overall length of the prosthesis 96. The uncovered wire cage 46 may reside at only a single end of the prosthesis 96, such as for traversing the renal arteries. Alternatively, exposed portions of the wire cage 46 may be provided at both ends of the prosthesis such as for anchoring purposes.

In a further alternative, a two part polymeric sleeve 44 is provided. A first distal part spans the aneurysm 40, and has a proximal end which terminates distally of the renal arteries. A second, proximal part of the polymeric sleeve 44 is carried by the proximal portion of the wire cage 46 which is positioned superiorly of the renal arteries. This leaves an annular lateral flow path through the side wall of the vascular prosthesis 96, which can be axially aligned with the renal arteries, without regard to rotational orientation.

The axial length of the gap between the proximal and distal segments of polymeric sleeve 44 can be adjusted, depending upon the anticipated cross-sectional size of the ostium of the renal artery, as well as the potential axial misalignment between the right and left renal arteries. Although the right renal artery 32 and left renal artery 34 are illustrated in FIG. 16 as being concentrically disposed on opposite sides of the abdominal aorta, the take off point for the right or left renal arteries from the abdominal aorta may be spaced apart along the abdominal aorta as will be familiar to those of skill in the art. In general, the diameter of the ostium of the renal artery measured in the axial direction along the abdominal aorta falls within the range of from about 7 mm to about 20 mm for a typical adult patient.

Prior art procedures presently use a 7 mm introducer (18 French) which involves a surgical procedure for introduction of the graft delivery device. Embodiments of the present invention can be constructed having a 16 French or 15 French or 14 French or smaller profile (e.g. 3–4 mm) thereby enabling placement of the endoluminal vascular prosthesis of the present invention by way of a percutaneous procedure. In addition, the endoluminal vascular prosthesis of the present invention does not require a post implantation balloon dilatation, can be constructed to have minimal axial shrinkage upon radial expansion.

Referring to FIG. 17, there is disclosed a schematic representation of the abdominal part of the aorta and its principal branches as in FIG. 1. An expanded bifurcated endoluminal vascular prosthesis 102, in accordance with the present invention, is illustrated spanning the aneurysms 103, 104 and 105. The endoluminal vascular prosthesis 102 includes a polymeric sleeve 106 and a tubular wire support 107, which are illustrated in situ in FIG. 17. The sleeve 106 and wire support 107 are more readily visualized in the exploded view shown in FIG. 19. The endoluminal prosthesis 102 illustrated and described herein depicts an embodiment in which the polymeric sleeve 106 is situated concentrically outside of the tubular wire support 107. However, other embodiments may include a sleeve situated instead concentrically inside the wire support or on both of the inside and the outside of the wire support. Alternatively, the wire support may be embedded within a polymeric matrix which makes up the sleeve. Regardless of whether the sleeve 106 is inside or outside the wire support 107, the sleeve may be attached to the wire support by any of a variety of means, as has been previously discussed.

The tubular wire support 107 comprises a primary component 108 for traversing the aorta and a first iliac, and a branch component 109 for extending into the second iliac. The primary component 108 may be formed from a continuous single length of wire, throughout both the aorta trunk portion and the iliac branch portion. See FIGS. 19 and 20. Alternatively, each iliac branch component can be formed separately from the aorta trunk portion. Construction of the graft from a three part cage conveniently facilitates the use of different gauge wire in the different components (e.g. 14 gauge main trunk and 10 gauge branch components).

Figure 20:
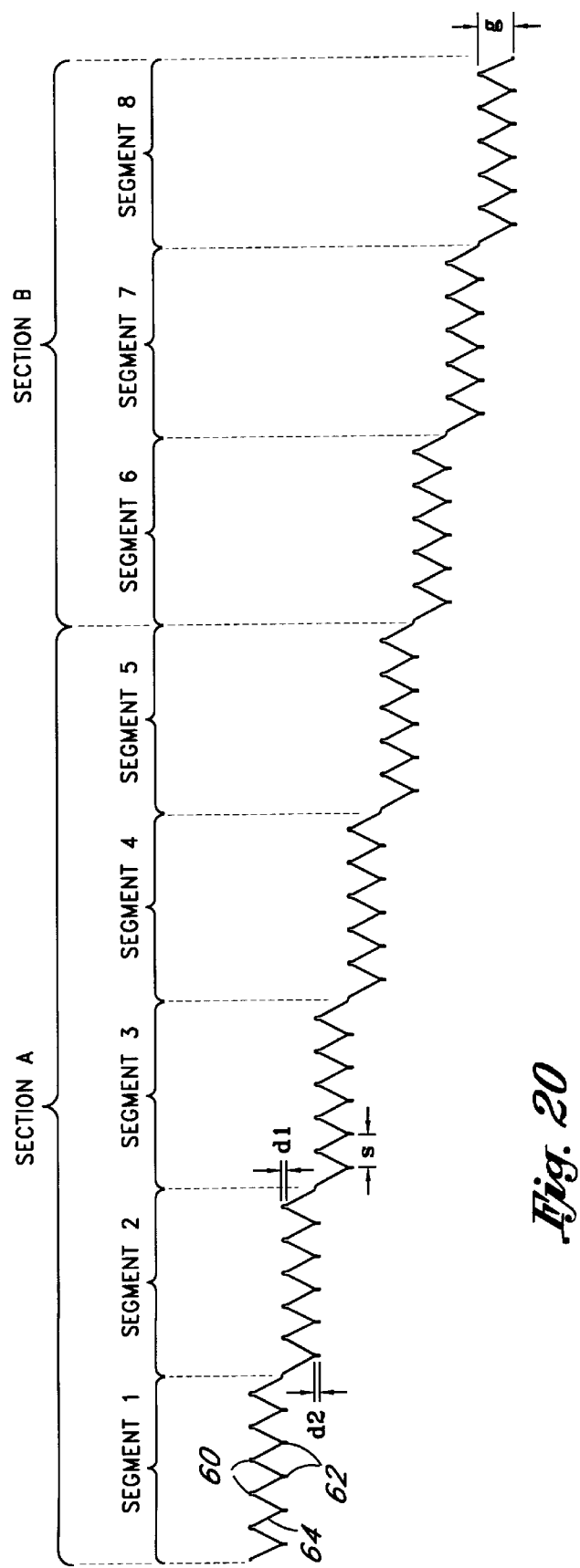
FIG. 20 is a plan view of formed wire useful for rolling about an axis into an aortic trunk segment and a first iliac branch segment support structure in accordance with the present invention.

The wire support 107 is preferably formed in a plurality of discrete segments, connected together and oriented about a common axis. In FIG. 20, Section A corresponds to the aorta trunk portion of the primary component 108, and includes segments 1–5. Segments 6–8 (Section B) correspond to the iliac branch portion of the primary component 108.

In general, each of the components of the tubular wire support 107 can be varied considerably in diameter, length, and expansion coefficient, depending upon the intended application. For implantation within a typical adult, the aorta trunk portion (section A) of primary component 108 will have a length within the range of from about 5 cm to about 12 cm, and, typically within the range of from about 9 cm to about 10 cm. The unconstrained outside expanded diameter of the section A portion of the primary component 108 will typically be within the range of from about 20 mm to about 40 mm. The unconstrained expanded outside diameter of the section A portion of primary component 108 can be constant or substantially constant throughout the length of section A, or can be tapered from a relatively larger diameter at the proximal end to a relatively smaller diameter at the bifurcation. In general, the diameter of the distal end of section A will be on the order of no more than about 95% and, preferably, no more than about 85% of the diameter of the proximal end of section A.

The right and left iliac portions, corresponding to section B on primary component 108 and section C will typically be bilaterally symmetrical. Section C length will generally be within the range of from about 1 cm to about 5 cm, and section C diameter will typically be within the range of from about 10 mm to about 20 mm.

Referring to FIG. 19, the wire cage 107 is dividable into a proximal zone 110, a central zone 111 and a distal zone 112. As has been discussed, the wire cage 107 can be configured to taper from a relatively larger diameter in the proximal zone 110 to a relatively smaller diameter in the distal zone 112. In addition, the wire cage 107 can have a transitional tapered and or stepped diameter within a given zone.

The wire may be made from any of a variety of different alloys and wire diameters or nonround cross-sections, as has been discussed. In one embodiment of the bifurcation graft, the wire gauge remains substantially constant throughout section A of the primary component 49 and steps down to a second, smaller cross-section throughout section B of primary component 108.

A wire diameter of approximately 0.018 inches may be useful in the aorta trunk portion of a graft having five segments each having 2.0 cm length per segment, each segment having six struts intended for use in the aorta, while a smaller diameter such as 0.012 inches might be useful for segments of the graft having 6 struts per segment intended for the iliac artery.

In one embodiment of the present invention, the wire diameter may be tapered throughout from the proximal to distal ends of the section A and/or section B portions of the primary component 108. Alternatively, the wire diameter may be tapered incremental or stepped down, or stepped up, depending on the radial strength requirements of each particular clinical application. In one embodiment, intended for the abdominal aortic artery, the wire has a cross-section of about 0.018 inches in the proximal zone 110 and the wire tapers down regularly or in one or more steps to a diameter of about 0.012 inches in the distal zone 112 of the graft 102. End point dimensions and rates of taper can be varied widely, within the spirit of the present invention, depending upon the desired clinical performance.

In general, in the tapered or stepped wire embodiments, the diameter of the wire in the iliac branches is no more than about 80% of the diameter of the wire in the aortic trunk. This permits increased flexibility of the graft in the region of the iliac branches, which has been determined by the present inventors to be clinically desirable.

Referring to FIG. 20, there is illustrated a plan view of the single formed wire used for rolling about a longitudinal axis to produce a primary segment 108 having a five segment aorta section and a three segment iliac section. The formed wire exhibits distinct segments, each corresponding to an individual tubular segment in the tubular support. Additional details of the wire cage layout and construction can be found in copending U.S. patent application Ser. No. 09/034,689 entitled Endoluminal Vascular Prosthesis, filed Mar. 4, 1998, the disclosure of which is incorporated in its entirety herein by reference.

Each segment has a repeating pattern of proximal bends 60 connected to corresponding distal bends 62 by wall sections 64 which extend in a generally zig zag configuration when the segment is radially expanded, as has been discussed in connection with FIG. 3. Each segment is connected to the adjacent segment through a connector 66, and one or more links 70 as has been discussed in connection with FIGS. 5–12. The connector 66 in the illustrated embodiment comprises two wall sections 64 which connect a proximal bend 60 on a first segment with a distal bend 62 on a second, adjacent segment. The connector 66 may additionally be provided with a connector bend 68, which may be used to impart increased radial strength to the graft and/or provide a tie site for a circumferentially extending suture.

In the illustrated embodiment, section A is intended for deployment within the aorta whereas section B is intended to be deployed within a first iliac. Thus, section B will preferably have a smaller expanded diameter than section A. This may be accomplished by providing fewer proximal and distal bends 60, 62 per segment in section B or in other manners as will be apparent to those of skill in the art in view of the disclosure herein. In the illustrated embodiment, section B has one fewer proximal bend 60 per segment than does each segment in section A. This facilitates wrapping of the wire into a tubular prosthesis cage such as that illustrated in FIG. 19, so that the iliac branch has a smaller diameter than the aorta branch. At the bifurcation, an opening remains for connection of the second iliac branch. The second branch is preferably formed from a section of wire in accordance with the general principles discussed above, and in a manner that produces a similarly dimensioned wire cage as that produced by section B. The second iliac branch (section C) may be attached at the bifurcation to section A and/or section B in any of a variety of manners, to provide a secure junction therebetween. In one embodiment, one or two of the proximal bends 60 on section C will be secured to the corresponding distal bends 62 on the distal most segment of section A. Attachment may be accomplished such as through the use of a circumferentially threaded suture, through links 70 as has been discussed previously, through soldering or other attachment means. The attachment means will be influenced by the desirable flexibility of the graft at the bifurcation, which will in turn be influenced by the method of deployment of the vascular graft as will be apparent to those of skill in the art in view of the disclosure herein.

The collapsed prosthesis in accordance with the present invention has a diameter in the range of about 2 to about 10 mm. Preferably, the maximum diameter of the collapsed prosthesis is in the range of about 3 to 6 mm (12 to 18 French). Some embodiments of the delivery catheter including the prosthesis will be in the range of from 18 to 20 or 21 French; other embodiments will be as low as 19 F, 16 F, 14 F, or smaller. After deployment, the expanded endoluminal vascular prosthesis has radially self-expanded to a diameter anywhere in the range of about 20 to 40 mm, corresponding to expansion ratios of about 1:2 to 1:20. In a preferred embodiment, the expansion ratios range from about 1:4 to 1:8, more preferably from about 1:4 to 1:6.

The self expandable bifurcation graft of the present invention can be deployed at a treatment site in accordance with any of a variety of techniques as will be apparent to those of skill in the art. One such technique is disclosed in copending patent application Ser. No. 08/802,478 entitled Bifurcated Vascular Graft and Method and Apparatus for Deploying Same, filed Feb. 20, 1997, the disclosure of which is incorporated in its entirety herein by reference.

A partial cross-sectional side elevational view of one deployment apparatus 120 in accordance with the present invention is shown in FIG. 21. The deployment apparatus 120 comprises an elongate flexible multicomponent tubular body 122 having a proximal end 124 and a distal end 126. The tubular body 122 and other components of this system can be manufactured in accordance with any of a variety of techniques well known in the catheter manufacturing field. Suitable materials and dimensions can be readily selected taking into account the natural anatomical dimensions in the iliacs and aorta, together with the dimensions of the desired percutaneous access site.

The elongate flexible tubular body 122 comprises an outer sheath 128 which is axially movably positioned upon an intermediate tube 130. A central tubular core 132 is axially movably positioned within the intermediate tube 130. In one embodiment, the outer tubular sheath comprises extruded PTFE, having an outside diameter of about 0.250" and an inside diameter of about 0.230". The tubular sheath 128 is provided at its proximal end with a manifold 134, having a hemostatic valve 136 thereon and access ports such as for the infusion of drugs or contrast media as will be understood by those of skill in the art.

The outer tubular sheath 128 has an axial length within the range of from about 40" to about 55", and, in one embodiment of the deployment device 120 having an overall length of 110 cm, the axial length of the outer tubular sheath 128 is about 52 cm and the outside diameter is no more than about 0.250". Thus, the distal end of the tubular sheath 128 is located at least about 16 cm proximally of the distal end 126 of the deployment catheter 120 in stent loaded configuration.

As can be seen from FIGS. 22 and 25–26, proximal retraction of the outer sheath 128 with respect to the intermediate tube 130 will expose the compressed iliac branches of the graft, as will be discussed in more detail below.

A distal segment of the deployment catheter 120 comprises an outer tubular housing 138, which terminates distally in an elongate flexible tapered distal tip 140. The distal housing 138 and tip 140 are axially immovably connected to the central core 132 at a connection 142.

The distal tip 140 preferably tapers from an outside diameter of about 0.225" at its proximal end to an outside diameter of about 0.070" at the distal end thereof. The overall length of the distal tip 140 in one embodiment of the deployment catheter 120 is about 3". However, the length and rate of taper of the distal tip 140 can be varied depending upon the desired trackability and flexibility characteristics. The distal end of the housing 138 is secured to the proximal end of the distal tip 140 such as by thermal bonding, adhesive bonding, and/or any of a variety of other securing techniques known in the art. The proximal end of distal tip 140 is preferably also directly or indirectly connected to the central core 132 such as by a friction fit and/or adhesive bonding.

In at least the distal section of the catheter, the central core 132 preferably comprises a length of hypodermic needle tubing. The hypodermic needle tubing may extend throughout the length catheter to the proximal end thereof, or may be secured to the distal end of a proximal extrusion as illustrated for example in FIG. 22. A central guidewire lumen 144 extends throughout the length of the tubular central core 132, having a distal exit port 146 and a proximal access port 148 as will be understood by those of skill in the art.

Referring to FIGS. 22–24, a bifurcated endoluminal graft 150 is illustrated in a compressed configuration within the deployment catheter 120. The graft 150 comprises a distal aortic section 152, a proximal ipsilateral iliac portion 154, and a proximal contralateral iliac portion 156. The aortic trunk portion 152 of the graft 150 is contained within the tubular housing 138. Distal axial advancement of the central tubular core 132 will cause the distal tip 140 and housing 138 to advance distally with respect to the graft 150, thereby permitting the aortic trunk portion 152 of the graft 150 to expand to its larger, unconstrained diameter. Distal travel of the graft 150 is prevented by a distal stop 158 which is axially immovably connected to the intermediate tube 130. Distal stop 158 may comprise any of a variety of structures, such as an annular flange or component which is adhered to, bonded to or intregally formed with a tubular extension 160 of the intermediate tube 132. Tubular extension 160 is axially movably positioned over the hypotube central core 132.

The tubular extension 160 extends axially throughout the length of the graft 150. At the proximal end of the graft 150, a step 159 axially immovably connects the tubular extension 160 to the intermediate tube 130. In addition, the step 159 provides a proximal stop surface to prevent proximal travel of the graft 150 on the catheter 120. The function of step 159 can be accomplished through any of a variety of structures as will be apparent to those of skill in the art in view of the disclosure herein. For example, the step 159 may comprise an annular ring or spacer which receives the tubular extension 160 at a central aperture therethrough, and fits within the distal end of the intermediate tube 130. Alternatively, the intermediate tube 130 can be reduced in diameter through a generally conical section or shoulder to the diameter of tubular extension 160.

Proximal retraction of the outer sheath 128 will release the iliac branches 154 and 156 of the graft 150. The iliac branches 154 and 156 will remain compressed, within a first (ipsilateral) tubular sheath 162 and a second (contralateral) tubular sheath 164. The first tubular sheath 162 is configured to restrain the ipsilateral branch of the graft 150 in the constrained configuration, for implantation at the treatment site. The first tubular sheath 162 is adapted to be axially proximally removed from the iliac branch, thereby permitting the branch to expand to its implanted configuration. In one embodiment, the first tubular sheath 162 comprises a thin walled PTFE extrusion having an outside diameter of about 0.215" and an axial length of about 7.5 cm. A proximal end of the tubular sheath 162 is necked down such as by heat shrinking to secure the first tubular sheath 162 to the tubular extension 160. In this manner, proximal withdrawal of the intermediate tube 130 will in turn proximally advance the first tubular sheath 162 relative to the graft 150, thereby deploying the self expandable iliac branch of the graft 150.

The second tubular sheath 164 is secured to the contralateral guidewire 166, which extends outside of the tubular body 122 at a point 168, such as may be conveniently provided at the junction between the outer tubular sheath 128 and the distal housing 138. The second tubular sheath 164 is adapted to restrain the contralateral branch of the graft 150 in the reduced profile. In one embodiment of the invention, the second tubular sheath 164 has an outside diameter of about 0.215" and an axial length of about 7.5 cm. The second tubular sheath 164 can have a significantly smaller cross-section than the first tubular sheath 162, due to the presence of the tubular core 132 and intermediate tube 130 within the first iliac branch 154.

The second tubular sheath 164 is secured at its proximal end to a distal end of the contralateral guidewire 166. This may be accomplished through any of a variety of securing techniques, such as heat shrinking, adhesives, mechanical interfit and the like. In one embodiment, the guidewire is provided with a knot or other diameter enlarging structure to provide an interference fit with the proximal end of the second tubular sheath 156, and the proximal end of the second tubular sheath 156 is heat shrunk and/or bonded in the area of the knot to provide a secure connection. Any of a variety of other techniques for providing a secure connection between the contralateral guidewire 166 and tubular sheath 156 can readily be used in the context of the present invention as will be apparent to those of skill in the art in view of the disclosure herein. The contralateral guidewire 166 can comprise any of a variety of structures, including polymeric monofilament materials, braided or woven materials, metal ribbon or wire, or conventional guidewires as are well known in the art.

In use, the free end of the contralateral guidewire 166 is percutaneously inserted into the arterial system, such as at a first puncture in a femoral artery. The contralateral guidewire is advanced through the corresponding iliac towards the aorta, and crossed over into the contralateral iliac in accordance with cross over techniques which are well known in the art. The contralateral guidewire is then advanced distally down the contralateral iliac where it exits the body at a second percutaneous puncture site.

The deployment catheter 120 is thereafter percutaneously inserted into the first puncture, and advanced along a guidewire (e.g. 0.035 inch) through the ipsilateral iliac and into the aorta. As the deployment catheter 120 is transluminally advanced, slack produced in the contralateral guidewire 166 is taken up by proximally withdrawing the guidewire 166 from the second percutaneous access site. In this manner, the deployment catheter 120 is positioned in the manner generally illustrated in FIG. 25.

Figure 26:
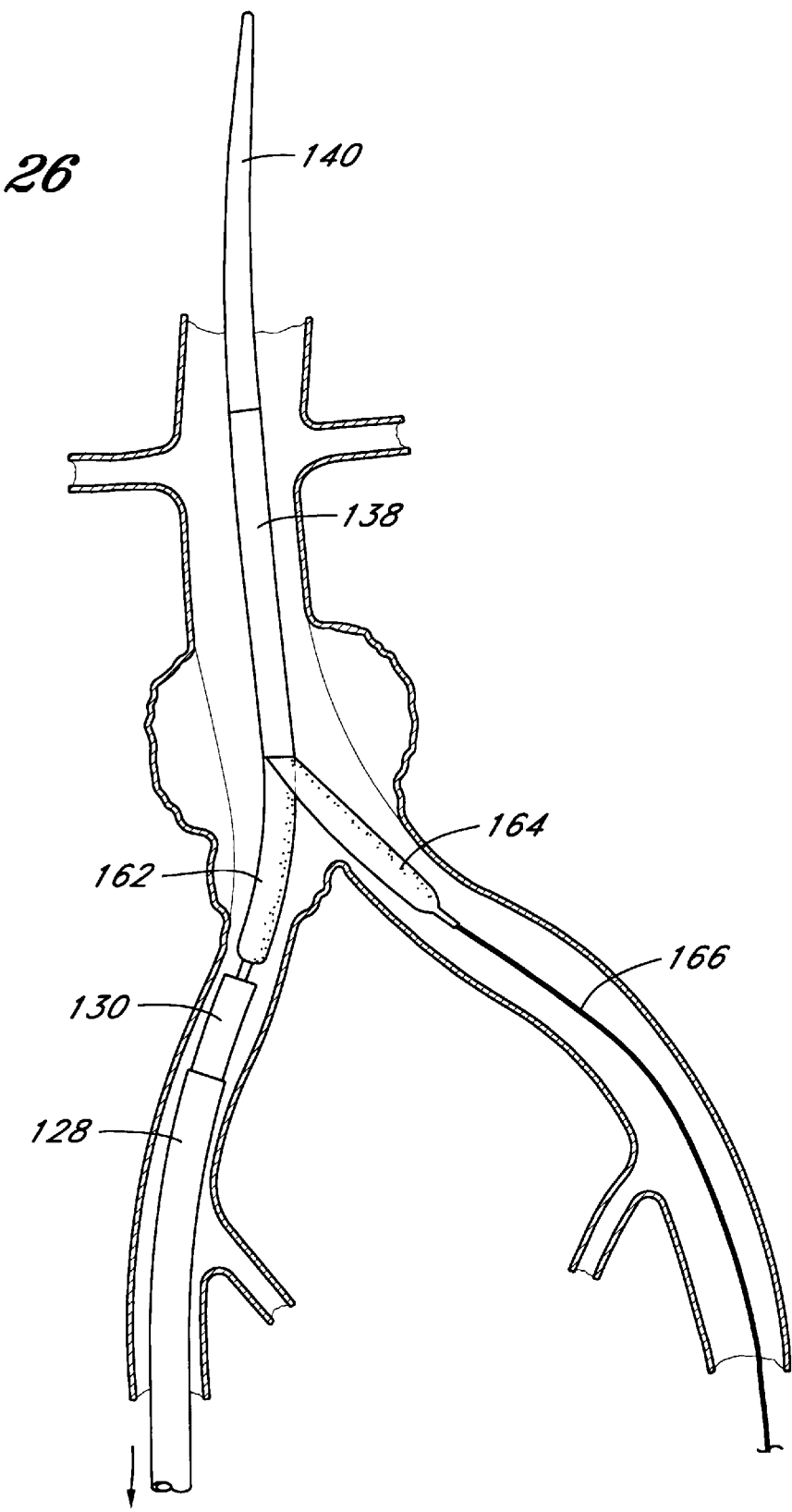
FIG. 26 is a schematic representation as in FIG. 25, with the outer sheath proximally retracted and the compressed iliac branches of the graft moving into position within the iliac arteries.

Referring to FIG. 26, the outer sheath 128 is proximally withdrawn while maintaining the axial position of the overall deployment catheter 120, thereby releasing the first and second iliac branches of the graft 150. Proximal advancement of the deployment catheter 120 and contralateral guidewire 166 can then be accomplished, to position the iliac branches of the graft 150 within the iliac arteries as illustrated.

Figure 27:
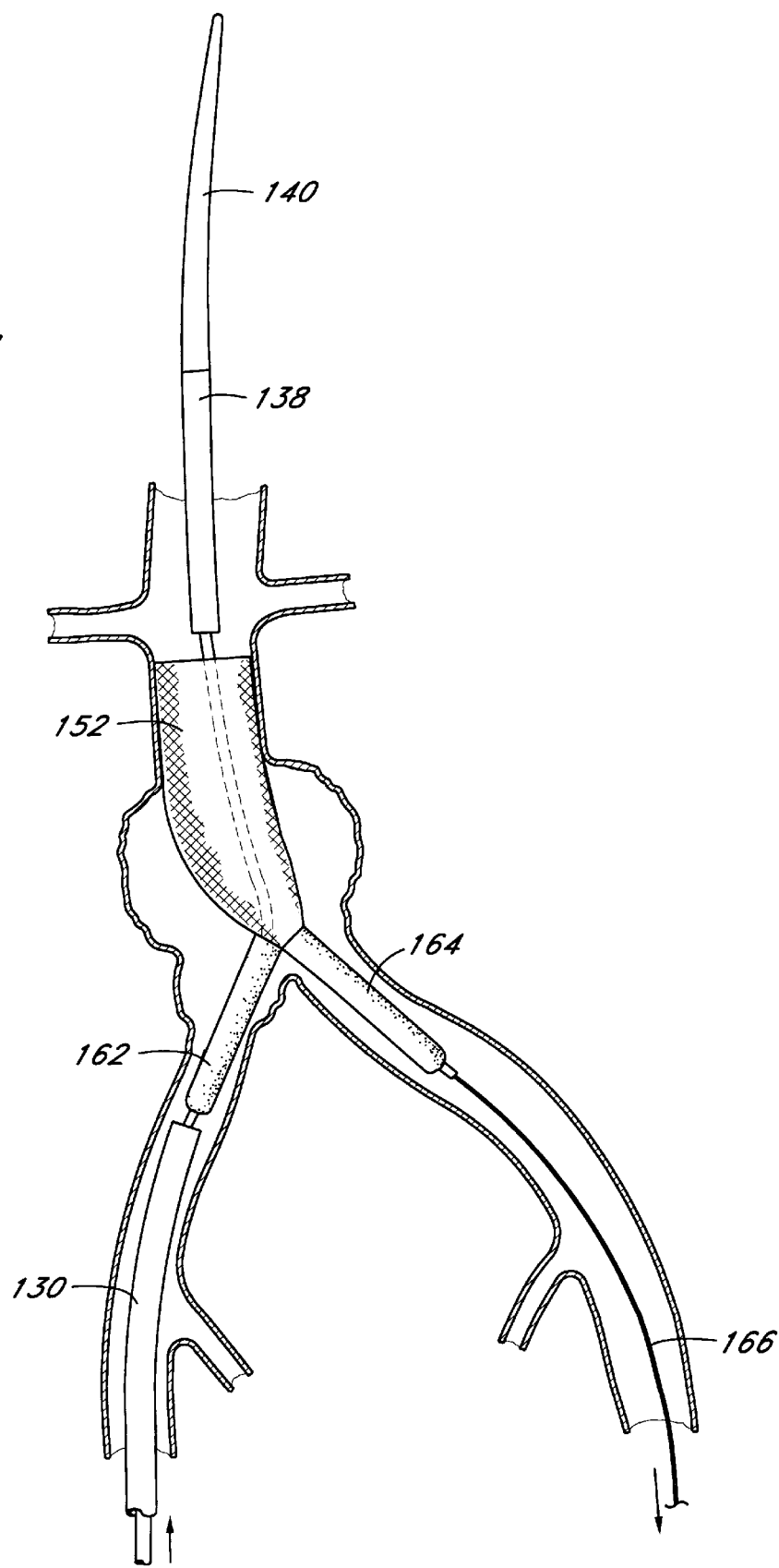
FIG. 27 is a schematic representation as in FIG. 26, with the compressed iliac branches of the graft within the iliac arteries, and the main aortic trunk of the graft deployed within the aorta.
Figure 28:
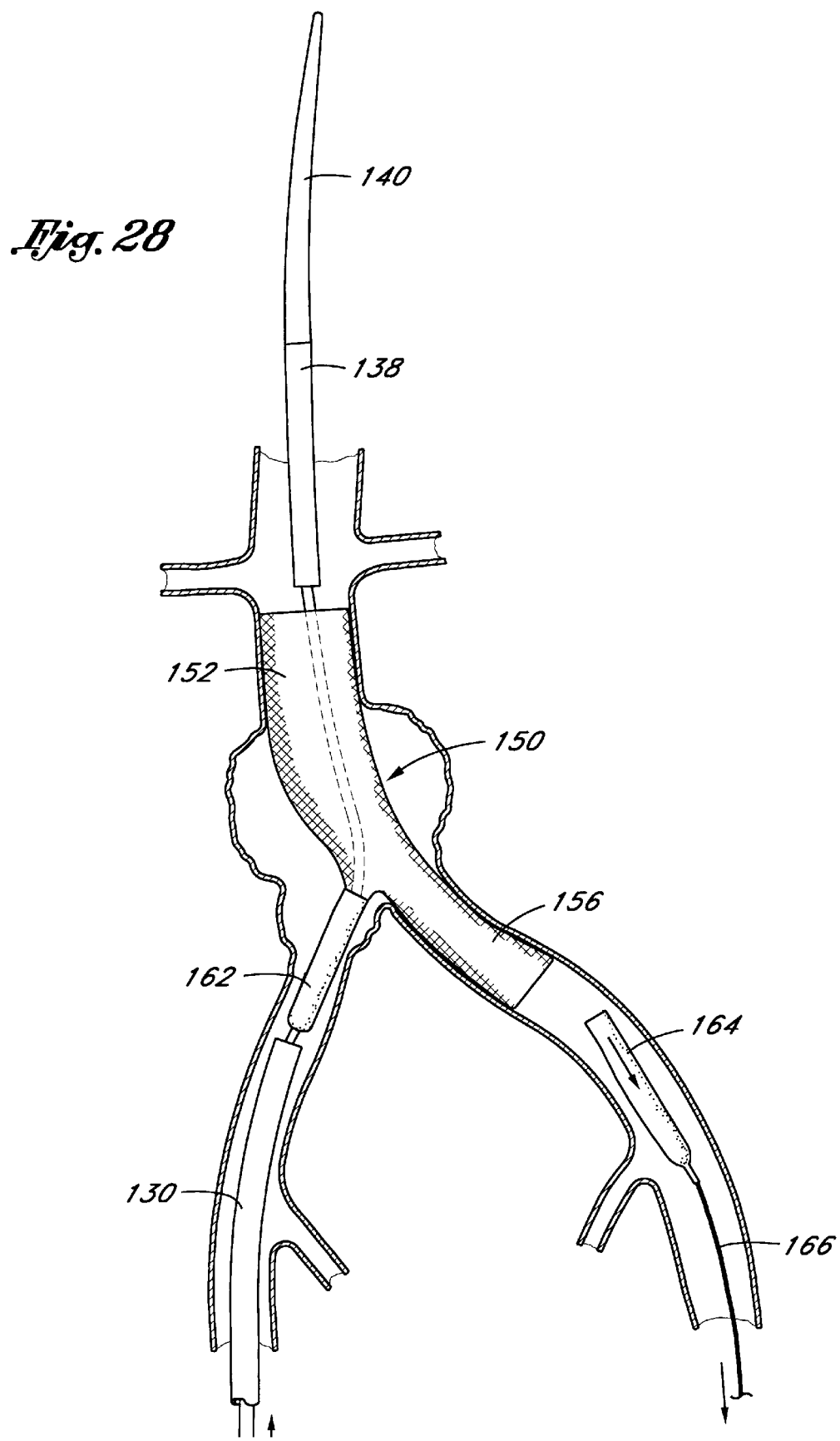
FIG. 28 is a schematic representation as in FIG. 27, with the contralateral iliac branch of the graft deployed.
Figure 29:
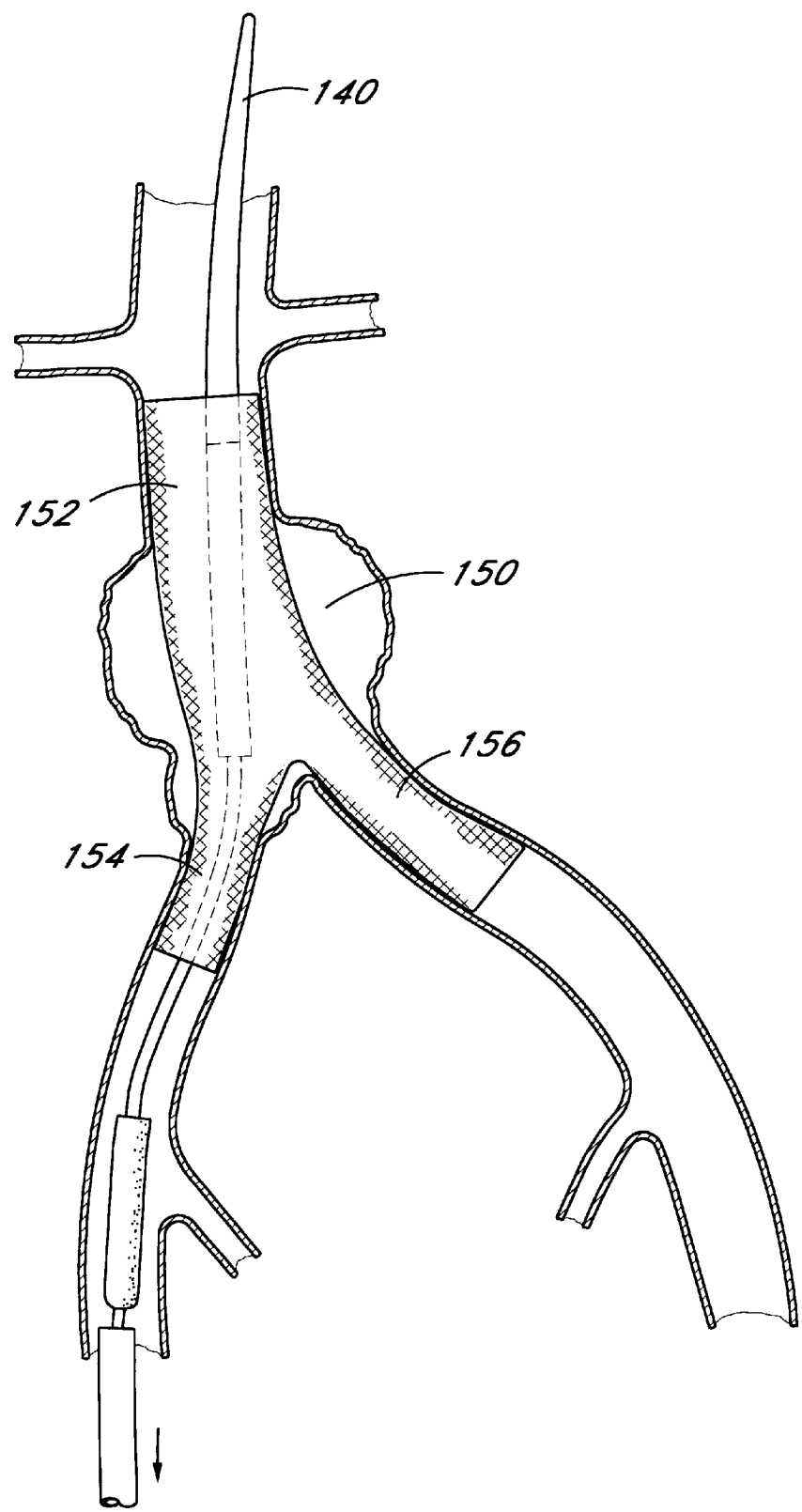
FIG. 29 is a schematic representation as in FIG. 28, following deployment of the ipsilateral branch of the graft.

Referring to FIG. 27, the central core 132 is distally advanced thereby distally advancing the distal housing 138 as has been discussed. This exposes the aortic trunk of the graft 150, which deploys into its fully expanded configuration within the aorta. As illustrated in FIG. 28, the contralateral guidewire 166 is thereafter proximally withdrawn, thereby by proximally withdrawing the second sheath 164 from the contralateral iliac branch 156 of the graft 150. The contralateral branch 156 of the graft 150 thereafter self expands to fit within the iliac artery. The guidewire 166 and sheath 164 may thereafter be proximally withdrawn and removed from the patient, by way of the second percutaneous access site.

Thereafter, the deployment catheter 120 may be proximally withdrawn to release the ipsilateral branch 154 of the graft 150 from the first tubular sheath 162. Following deployment of the ipsilateral branch 154 of the prosthesis 150, a central lumen through the aortic trunk 152 and ipsilateral branch 154 is sufficiently large to permit proximal retraction of the deployment catheter 120 through the deployed bifurcated graft 150. The deployment catheter 120 may thereafter be proximally withdrawn from the patient by way of the first percutaneous access site.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. A method of making an endoluminal prosthesis, comprising the steps of:

providing a length of wire;

forming the wire into at least two zig-zag sections having proximal and distal apexes;

rolling the formed wire about an axis to produce at least two tubular elements positioned along the axis such that at least one proximal apex on one element axially overlaps with a distal apex on a second element;

folding one of the proximal or distal apex through the overlapping proximal or distal apex to produce a folded link; and closing the folded link such that the folded apex forms a functionally closed aperture which substantially entraps the overlapping apex.

2. A method as in claim 1, further comprising the step of positioning a tubular polymeric sleeve concentrically on at least one of the tubular elements.

3. A method as in claim 2, wherein the positioning step comprises positioning the tubular polymeric sleeve concentrically on the outside surface of the tubular element.

4. A method as in claim 3, wherein the tubular polymeric sleeve comprises PTFE.

5. A movable link for securing two portions of the wall of a tubular endovascular prosthesis, comprising:

a first wire portion having two side-by-side legs and an apex thereon; and a second wire portion adjacent the first wire portion;

wherein the first wire portion is wrapped around the second wire portion to form a functionally closed aperture, wherein the second wire portion is substantially entrapped within the aperture.

* * * * *